(12) United States Patent
Wetzel et al.

(10) Patent No.: US 10,575,726 B2
(45) Date of Patent: Mar. 3, 2020

(54) AUTOMATED ANALYSIS SYSTEM FOR THE DETECTION AND SCREENING OF NEUROLOGICAL DISORDERS AND DEFECTS

(71) Applicant: VIRGINIA COMMONWEALTH UNIVERSITY, Richmond, VA (US)

(72) Inventors: Paul A. Wetzel, Richmond, VA (US); Mark S. Baron, Richmond, VA (US); George T. Gitchel, Richmond, VA (US)

(73) Assignee: VIRGINIA COMMONWEALTH UNIVERSITY, Richmond, VA (US)

( * ) Notice: Subject to any disclaimer, the term of this patent is extended or adjusted under 35 U.S.C. 154(b) by 662 days.

(21) Appl. No.: 14/774,152

(22) PCT Filed: Mar. 12, 2014

(86) PCT No.: PCT/US2014/023923
§ 371 (c)(1),
(2) Date: Sep. 10, 2015

(87) PCT Pub. No.: WO2014/159498
PCT Pub. Date: Oct. 2, 2014

(65) Prior Publication Data
US 2016/0022137 A1    Jan. 28, 2016

Related U.S. Application Data

(60) Provisional application No. 61/783,156, filed on Mar. 14, 2013.

(51) Int. Cl.
*A61B 3/113*   (2006.01)
*A61B 5/00*   (2006.01)
*A61B 5/11*   (2006.01)

(52) U.S. Cl.
CPC ............ *A61B 3/113* (2013.01); *A61B 5/1103* (2013.01); *A61B 5/4076* (2013.01);
(Continued)

(58) Field of Classification Search
None
See application file for complete search history.

(56) References Cited

U.S. PATENT DOCUMENTS

2002/0099305 A1   7/2002   Fukushima et al.
2003/0065535 A1*   4/2003   Karlov ................. G06Q 50/22
                                                         705/2
(Continued)

OTHER PUBLICATIONS

C. Helmchen, A. Hagenow, J. Miesner, A. Sprenger, H. Rambold, R. Wenzelburger, W. Heide, G. Deuschl; Eye movement abnormalities in essential tremor may indicate cerebellar dysfunction, Brain, vol. 126, Issue 6, Jun. 1, 2003, pp. 1319-1332.*
(Continued)

*Primary Examiner* — Devin B Henson
*Assistant Examiner* — Benjamin S Melhus
(74) *Attorney, Agent, or Firm* — W & C IP

(57) ABSTRACT

Objects of interest which project beyond the fovea are poorly resolved and lack color information, requiring movement of the eyes in order to obtain a comprehensive image and perception of the surrounding world. Eye movements emanate from different areas of the brain which can be affected by disease and or injury. As such, different neurological disorders will affect a myriad of eye movements in a variety of different ways. An automated system and method, capable of detecting, analyzing and summarizing a person's eye movements is used to detect (diagnose) (either before or after symptoms of said neurological disease are apparent), confirm a prior diagnosis, and/or to monitor the treatment effectiveness for a variety of neurological diseases, neurological movement disorders and potential brain (Continued)

injuries. The analyzed and summarized eye movements are cataloged, interpreted and utilized in a diagnostic matrix in order to highlight and distinguish abnormal eye movements, and to provide an objective clinical or pre-clinical/pre-symptomatic diagnosis based on the non-invasive testing procedures.

8 Claims, 13 Drawing Sheets

(52) U.S. Cl.
CPC .......... *A61B 5/4082* (2013.01); *A61B 5/4842* (2013.01); *A61B 5/4848* (2013.01); *A61B 5/7257* (2013.01)

(56) References Cited

U.S. PATENT DOCUMENTS

| | | |
|---|---|---|
| 2009/0036755 A1 | 2/2009 | Anantha et al. |
| 2010/0100001 A1 | 4/2010 | Aguilar et al. |
| 2010/0208205 A1 | 8/2010 | Tseng et al. |
| 2011/0043759 A1* | 2/2011 | Bushinsky ............. A61B 3/113 351/210 |
| 2012/0059282 A1 | 3/2012 | Agichtein et al. |
| 2014/0364761 A1* | 12/2014 | Benson ................ A61B 5/7267 600/558 |

OTHER PUBLICATIONS

Bolger C, Bojanic S, Sheahan NF, et al Ocular microtremor in patients with idiopathic Parkinson's disease Journal of Neurology, Neurosurgery & Psychiatry 1999;66:528-531.*

Incesu AI, Sobaci G. Malingering or simulation in ophthalmology-visual acuity. International Journal of Ophthalmology. 2011;4(5):558-566. doi:10.3980/j.issn.2222-3959.2011.05.19.*

Everling Munoz et al: "Look Away: The Anti-Saccade Task and the Voluntary Control of Eye Movement", Nature Reviews Neuroscience, vol. 5, pp. 218-228, Apr. 2004.

George T. Gitchel et al: "Utility of Eye Movement Tracking for the Differential Diagnosis of Movement Disorders", 63rd AAN Annual Meeting, Honolulu, HI, Apr. 9-16, 2011, Neurology vol. 76, issue 9, suppl. 4, A587, Mar. 1, 2011.

\* cited by examiner

AUTOMATED ANALYSIS SYSTEM FOR THE DETECTION AND SCREENING OF NEUROLOGICAL DISORDERS AND DEFECTS

CROSS-REFERENCE TO RELATED APPLICATIONS

This application claims priority to U.S. Provisional Patent Application Ser. No. 61/783,156, filed Mar. 14, 2013, and the complete contents thereof is herein incorporated by reference.

BACKGROUND

Field of the Invention

The invention is generally related to systems and methods which enable objective detection, confirmation, and/or evaluation of neurological disorders. More particularly, the invention utilizes the eye(s) of a subject as a window into the brain whereby eye movements are detected in response to various stimuli and, based on the eye movements, a rapid, painless, cost effective, accurate, and quantifiable diagnosis of neurological disorders is provided.

Description of the Prior Art

Monitoring a subject's response to light stimuli may be used to assess the subject's impairment of fitness. U.S. Pat. No. 5,422,690 to Rothberg, which is incorporated herein by reference, teaches a system whereby light stimuli are provided to a subject to cause the pupil to change size and the eye to move. Pupil diameter measurements are made of an image of the subject's pupil in response to on axis light stimuli, and eye tracking of the subject's eye in response to moving light stimuli is performed. The data acquired by measuring pupil diameter and saccadic movements of the subject's eye as a function of time are compared with baseline data for the subject. Deviations from baseline data are indicative of possible impairments from drugs or alcohol.

SUMMARY

Eye movements are necessary to position and orient the eye or eyes such that an object of interest falls upon the foveal area of the retina which possesses high visual acuity and receptors which are sensitive to color. Changes in the eye movements are indicative are neurological disorders. Embodiments of the invention include an automated method and system based on objective eye movement measurement and analysis for the early detection, diagnosis and measurement of treatment effectiveness for a variety of neurological diseases, neurological movement disorders and potential brain injuries. Preferably, automated algorithms and procedures are used to provide precise quantifiable measures of eye position behavior and oculomotor motility.

In an embodiment of the invention, an automated system and method, capable of detecting, analyzing and summarizing a person's eye movements is used to detect (diagnose), confine a prior diagnosis, and/or to monitor the treatment effectiveness (improvements with therapy being good progress, and non-improvement and or degradation with therapy being poor progress) for a variety of neurological diseases, neurological movement disorders and potential brain injuries. The analyzed and summarized eye movements are cataloged, interpreted and utilized in a diagnostic matrix in order to highlight and distinguish abnormal eye movements, and to provide an objective clinical diagnosis based on the non-invasive testing procedures.

A particular embodiment contemplates non-invasive quantifiable method for detecting changes in the brain caused by a variety of neurological diseases and disorders. Using an eye tracking device, the horizontal and vertical positions and pupillary size of one or both eyes of a patient are measured. A computer system takes the data output by the eye tracking device and performs a series of algorithms for the detection, identification and analysis of specific eye movement types and eye parameters. A decision matrix correlates eye measurement parameters detected or determined with likely neurological disorders or deficits. The types of neurological disorders or deficits include but are not limited to Parkinson's disease, essential tremor, Parkinson's disease plus essential tremor, small vessel ischemia, multiple system atrophy, progressive supranuclear palsy, cortical basal ganglionic degeneration, drug-induced tremor, normal pressure hydrocephalus, and malingering. Preprocessing may be performed to identify the existence of blinks and other artifacts which can be eliminated prior to analysis of the data.

In particular embodiments, position data can be differentiated to obtain a velocity signal, and can be differentiated again to obtain an acceleration signal. By applying minimum and maximum thresholds for velocity and acceleration, as well as to position change, the presence and precise time location of start and stop points of each saccadic eye movement can be detected and stored. Saccadic analysis is then performed to determine one or more of saccadic duration, peak saccadic velocity between saccadic start and stop times, peak acceleration at saccadic start, peak deceleration a saccadic stop, average velocity between saccadic start and stop time, and saccadic amplitude between saccadic start and stop times. Reading analysis for the subject may also be performed by storing a number and amplitude of left to right saccades and incrementing a first storage counter, storing a number and amplitude of right to left saccades and incrementing a second storage counter, storing an amplitude of return sweep and incrementing a third storage counter, storing fixation duration and incrementing a fourth storage counter, storing fixation stability measures, where intersaccadic interval defines behavior of the eye during periods of fixation and/or smooth pursuit eye movement, and storing reading speed measuring in words per minute (WPM) and characters per minute (CPM) and incrementing a fifth storage counter.

Intersaccadic interval analysis can be performed by first determining intersaccadic interval (ISI) based on time from end of previous saccade to start of next saccade, and then performing an analysis by, for example, determining one or more of mean eye position during intersaccadic interval, determining root mean square (RMS) eye position during IS, determining magnitude and direction of eye position during ISI (preferably with removal of offset bias), determining a mean velocity of eye during ISI, determining absolute mean eye velocity during ISI, determining RMS eye velocity during ISI, receiving target position and velocity and computing smooth pursuit gain where gain is equal to response velocity divided by target velocity, determining saccadic amplitude based on mean eye position before and after saccades, determining spectral components using discrete Fourier transform (DFT) analysis, and determining location and amplitude of saccadic intrusions.

DETAILED DESCRIPTION

When saccadic oscillations deviate from normal, this is indicative of unhealthy or not normal physical or psychological conditions. For example, nystagmus is characterized by a combination of slow phases which take the eye off the target, interspersed with saccade like quick phases that serve to bring the eye back to the target. Pathological slow phases may be due to either an imbalance in the vestibular system, damage to the brainstem, or other reasons. Ocular flutter is composed primarily fast phase saccadic eye movements.

Differences between eye movements cannot be easily discerned without precision instruments. Furthermore, a data set of multiple features for control subjects and a data set of multiple features for subjects suffering from various neurological disorders are required for discerning whether a patient is suffering from a particular neurological disorder.

Embodiments of this invention provide an objective method and system for the assessment of neurological disorders including potential injuries to the brain. In particular embodiments, the system and method will allow non-expert individuals and health care providers to, for example, prescreen and assess patients and individuals for a variety of neurological disorders based on an automated analysis of recorded eye movement behavior. Analyzed eye data may be presented to a decision tree based system which provides a likelihood estimator of potential disease state. A particular advantage of embodiments of the invention over currently available technology, is that it is capable of not only automatically analyzing eye movements, but also providing rapid accurate diagnosis with minimal time, effort, cost or discomfort to the patient or individual.

Exemplary uses of the system and method include without limitation the ability to provide early preclinical diagnosis of neurological movement disorders including mild head injuries and diagnosis prior to a patient being symptomatic of a neurological disease or disorder; confirming or refuting a patient's current diagnosis if there is a clinical uncertainty; and allowing clinicians to confirm a patient's diagnosis before therapeutic surgery takes place, thereby increasing surgical outcomes and saving money. Certain embodiments enable detecting preclinical stages of some movement disorders, potentially many years before the subject notices any outward symptoms, thereby allowing the patients to be started on effective neuroprotective therapies early, thereby improving the long term outlook for the patients.

Figure 1:
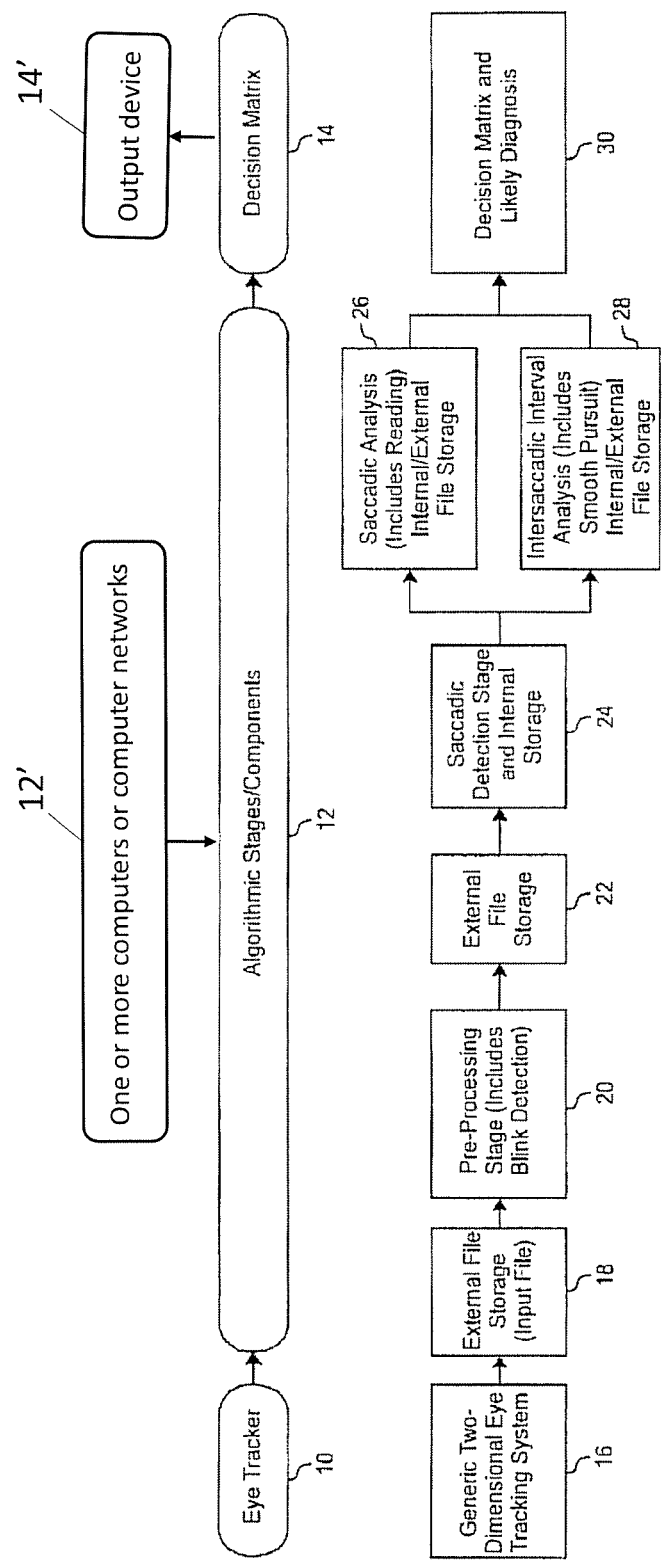
FIG. 1 is a schematic diagram illustrating the major components of an exemplary embodiment of the invention, and processes which are performed for identification or confirmation of particular neurological disorders.

With reference to FIG. 1, systems for practicing various embodiments of the invention are composed of three principle components. An eye tracker 10 is used to monitor the pupil size and gaze position of a subject's eye or eyes. In many embodiments, it is not necessary to record the position of both eyes, as the information need to assess an individual may be obtained from a single eye in many cases. However, when data from both eyes is used, this can increase the reliability of the system and method through correlation. Suitable eye tracker 10 devices are commercially available. For example, as shown in Examples 1 and 2 below, a video based binocular eye tracker referred to as Eyelink II, available from SR Research, Ltd., has been used in certain embodiments. Preferably, for many applications, the eye tracker 10 will be a two-dimensional eye tracking device capable of simultaneously measuring the horizontal and vertical positions and pupilary size of one or both eyes (the Eyelink II has these capabilities). The algorithmic stages/components 12 and decision matrix 14 may be embodied in the same computing or control device (processors), or each may be embodied in separate computing or control devices, or each may itself take the form of a network of computing devices. The algorithmic stages/components 12 is basically comprised of a series of algorithms for the detection, identification and analysis of specific eye movement types and eye parameters, as well as a method to remove artifact, noise, and blinks. The decision matrix 14 examines the correlation between the various eye measurement parameters and the likely neurological disorder or deficit.

FIG. 1 also illustrates a basic process flow and a breakdown of the system into various subcomponents. In particular, data collected using an eye tracker 10, such as a generic two dimensional eye tracking system 16 is collected in a storage device such as a database which may be, for example, an external file storage 18. This stored data constitutes an input file. Each scan session with a subject may generate one or more input files. In the algorithmic stages/components 12, a pre-processing stage 20 is used to process the data in the input file. The pre-processing stage 20 (which is discussed in more detail below in conjunction with FIG. 2) may include blink detection and other control systems or processing stages which eliminate extraneous data for analysis and/or identify pertinent data for analysis. This pre-processed data is then preferably stored in a suitable storage device 22 such as a database in for example an external file storage 22. In some embodiments, the external file storage 18 and external file storage 22 may be one and the same device, or they can each take the form of individual or multiple networked storage devices. It is necessary to be able to take the pre-processed data and analyze it by saccadic detection 24. This can be accomplished by storing the pre-processed data in the external file storage 22 as it is produced from the pre-processing stage 20, and retrieving this data at the saccadic detection stage 24, or simply by directing it directly from the pre-processing stage to the saccadic detection stage 24. After saccadic detection, one or both saccadic analysis 26 and intersaccadic interval analysis 28 may be performed. Output from these analyses may be stored in internal or external file storage for subsequent analysis (in some cases, processing of the analysis results may be performed at the same time as they analysis results are being obtained. The decision matrix 14 preferably provides a diagnosis 30 based on saccadic analysis and/or intersaccadic interval analysis.

Figure 2:
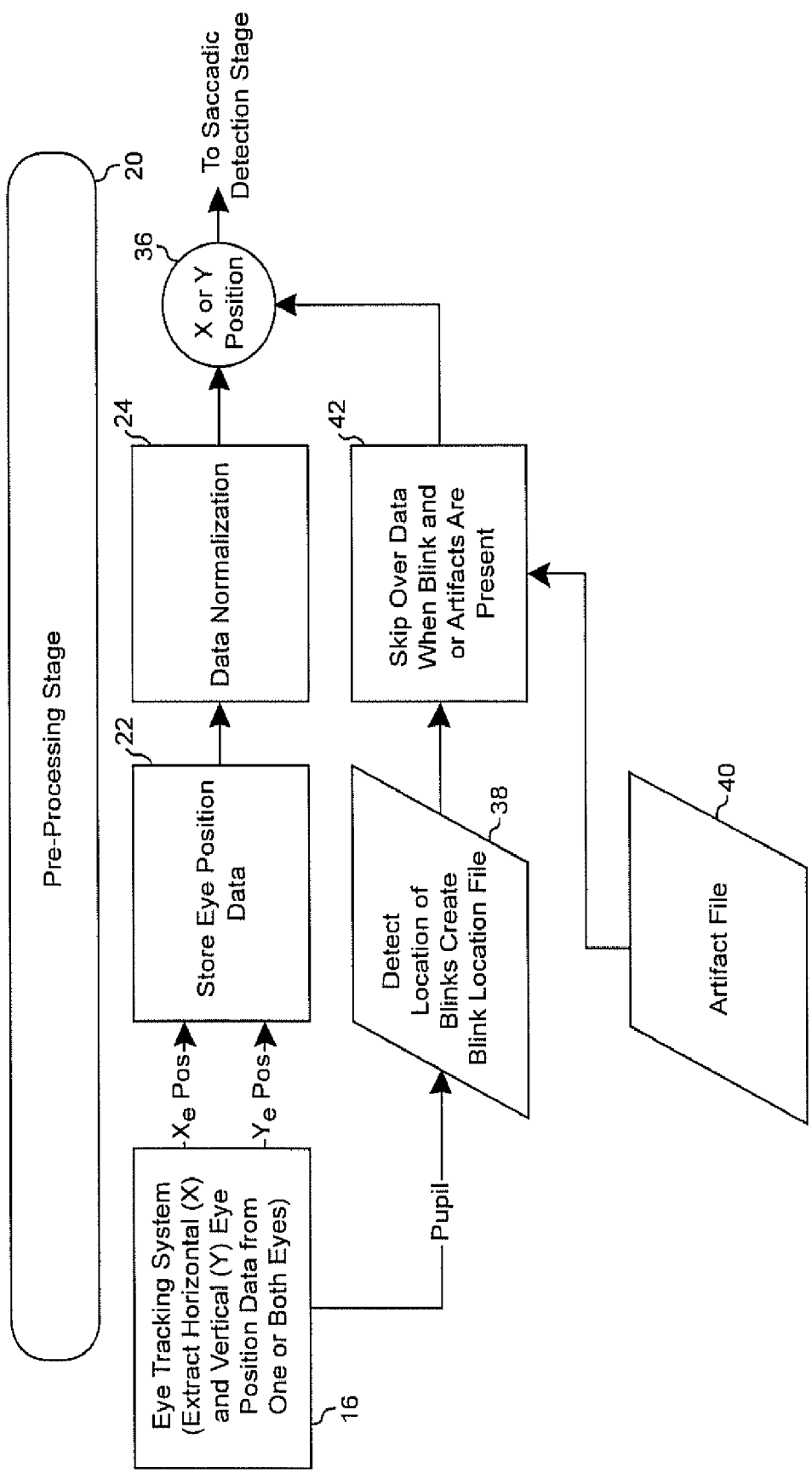
FIG. 2 is a schematic diagram illustrating an exemplary pre-processing stage of FIG. 1.

FIG. 2 shows the pre-processing stage 20 depicted in FIG. 1 preferably processes data recorded in file form from the eye tracking system and identifies the existence of blinks and any other artifacts that may be present before any being processed by the algorithms. This step prevents data with artifacts from being analyzed by the algorithms. The eye data is then presented to the saccadic detection stage. In FIG. 2, it can be seen that the eye tracking system 16 provides different types of outputs. For example, horizontal X and vertical Y position data for one or both eyes can be output to a storage stage 32 (e.g., database or file, etc.) which stores the eye position data (it is possible to store the coordinates together or separately, and, in the case of an eye tracker that only measures in the X or Y dimension to simply store the X or the Y data). Some of the data may include outliers, and there may be missing sample points. This can be addressed at a data normalization stage 34.

Figure 3:
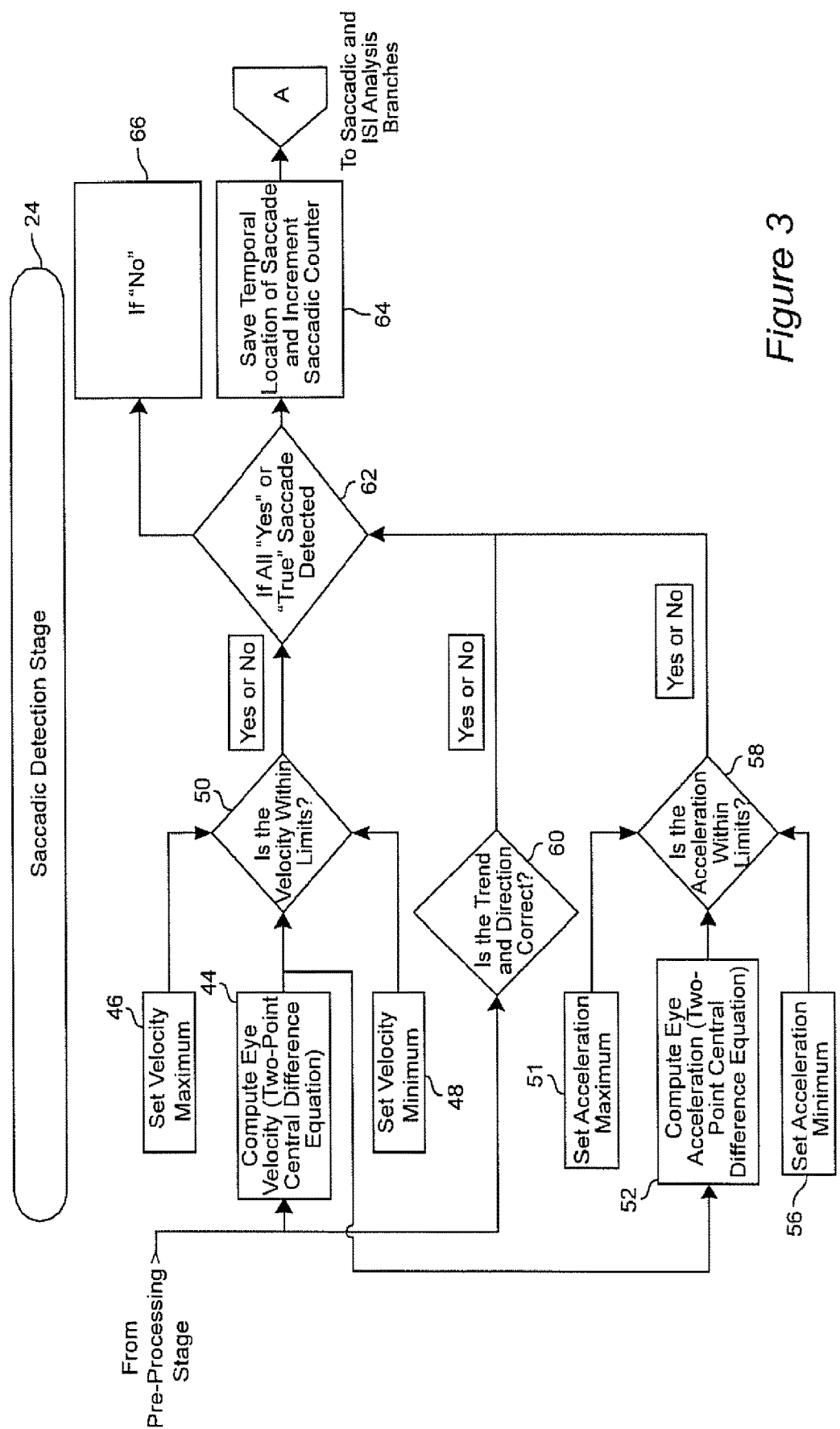
FIG. 3 is a schematic diagram illustrating an exemplary saccadic detection stage of FIG. 1.

FIG. 2 also shows accounting for blinks and other artifacts prior to passing X and/or Y position data 36 to the saccadic detection stage shown in FIG. 3. In particular, by monitoring the subject's pupil with the eye tracking system 16, the location of "blinks" in the collected data can be identified using a blink detection stage 38. The blink detection stage 38 identifies the location of blinks from data provided by the eye tracking system 16, and creates a blink location file. In addition, artifacts stored in an artifact file 40 are used to identify artifacts in the data from the eye tracking system 16. A "skip" stage 42 is used to skip over data when a blink and/or an artifact are present. Thus, the X and/or Y position data 36 provided to the saccadic detection stage will be adjusted to exclude any data which coincides with a blink and/or artifact.

Although not shown in FIG. 2, the eye tracking system 16 may also be used to make measurements of pupil diameter, and can be used to track the subject's pupil response to light stimulus or changes due to autonomic activity and changes due to target depth (vergence eye movements). This type of data may also be passed through a pre-processing stage 20 prior to further analysis.

FIG. 3 illustrates operations performed in the saccadic detection stage 24. At the saccadic detection stage 24, position data from the pre-processing stage (shown in FIG. 2) is differentiated at a compute eye velocity stage 44 to obtain a velocity signal using, for example, a two-point central difference method [see, e.g., Mathews J H, and Fink K K. (2004) *Numerical Methods Using Matlab* 4$^{th}$ Edition Prentice-Hall Inc. Upper Saddle River, N.J., USA]. This computed eye velocity is compared to a maximum set velocity 46 and a minimum set velocity 48 to determine if the computed velocity is within specified limits at step 50. Saccadic onset, or minimum velocity is experimentally derived, and generally set to 20°/s, although may be dynamically adjustable, while maximum velocity is used in combination with acceleration and position trends for blink detection. To obtain acceleration at step 52, the velocity signal computed at step 44 is differentiated again using a two-point central method. As with velocity, the computed eye acceleration is compared to maximum set acceleration limits 54 and minimum set acceleration limits 56 do determine whether the computed eye acceleration is within acceleration limits at step 58. Similar to velocity minima and maxima, values for acceleration are experimentally derived, and minima are generally set at 400°/s$^2$, whereas maximum values are used in conjunction with velocity and position trends to identify artifact or blinks. These thresholds may be dynamically adjusted in the case of neurological conditions that manifest extremely slow saccades that would be missed with static threshold values. Simultaneously, the position change of the eye is monitored to determine if the trend and direction of the detected point of focus for the subject's pupil is correct at step 60. While not shown in FIG. 3, minimum and maximums for position change of the eye are considered when analyzing the trend and direction. The predetermined and/or dynamically adjusted thresholds for the minimum position change, velocity, and acceleration are used to detect the presence and precise time location of the start and stop points of each saccade. As indicated in step 62, if the velocity is within limits, the acceleration is within limits, and the trend and direction are correct, a true saccade is detected. Each time a saccade is detected, the time location of the start and stop points will be stored, for example, in either internal or non-transient memory, at step 64 for saccadic and intersaccadic interval (ISI) analysis (see 26 and 28 in FIG. 1). If a true saccade is not detected, step 66 may start the process again and/or a process for detecting square wave jerks during fixation may proceed.

Figure 4:
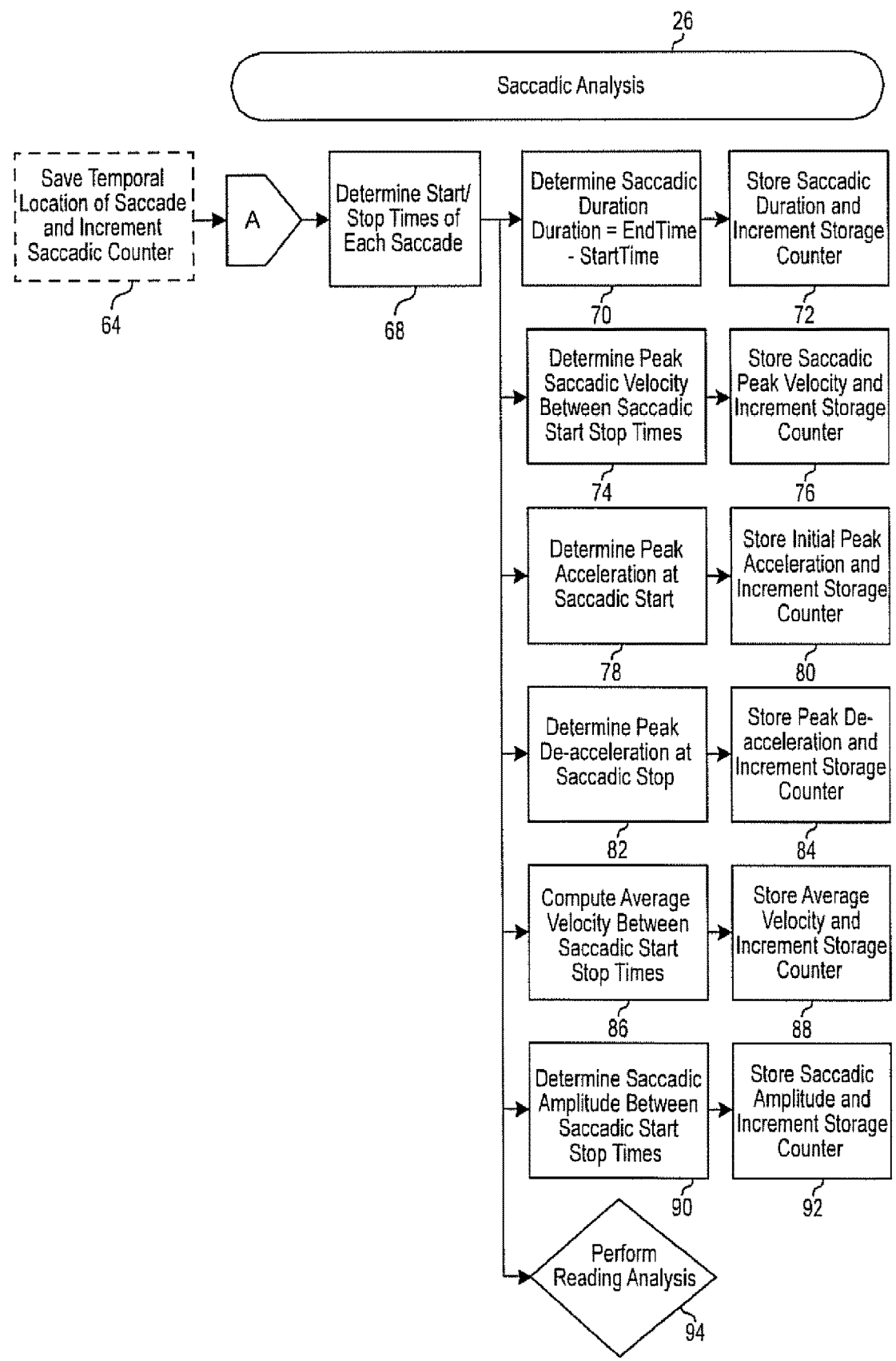
FIG. 4 is a schematic diagram illustrating an exemplary saccadic analysis stage of FIG. 1.

Given the locations determined in the saccadic detection stage 24, the numerous saccadic eye movement parameters as shown in the Saccadic Analysis Block Diagram of FIG. 4 can be calculated. Saccadic analysis can be performed by a variety of techniques [see, e.g., Leigh R J, and Zee D S. (2006) *The Neurology of Eye Movements*. Oxford University Press, New York, N.Y.]. In a particular embodiment illustrated in FIG. 4, data from the saved temporal location and increment saccadic counter 64 (see FIG. 3) is obtained, and the determined start/stop times of each saccade are retrieved or extracted at step 68 for analysis. From this data, various exemplary calculations may be performed including without limitation: a) the saccadic duration for any or each saccade can be determined by subtracting the start time from the end time at step 70 with the result being stored at step 72; b) the peak saccadic velocity can be determined between any or each saccadic start and stop times at step 74 with the peak saccadic velocity being stored at step 76; e) the peak acceleration at any or each saccadic start can be calculated at step 78 with the initial peak acceleration being stored at step 80; d) the peak de-acceleration at any or each saccadic stop can be calculated at step 82 and stored at step 84; e) the average velocity between saccadic start and stop times can be computed at step 86 and stored at step 88; and f) the saccadic amplitude between saccadic start and stop time can be computed at step 90 and stored at step 92. In various embodiments the stored saccadic duration, peak saccadic velocity, initial peak acceleration, peak de-acceleration, average velocity, and saccadic amplitude is correlated with the increment storage counter.

FIG. 4 also shows in some embodiments reading analysis 94 can be performed as part of a subroutine of the saccadic analysis stage 26. This enables analyzing reading performance as it correlates with eye movement analysis, e.g., a subject's reading speed might be analyzed and compared with their eye movements to diagnose physiological and/or psychological and/or neurological disorders, as well as making assessments on reading.

Figure 5:
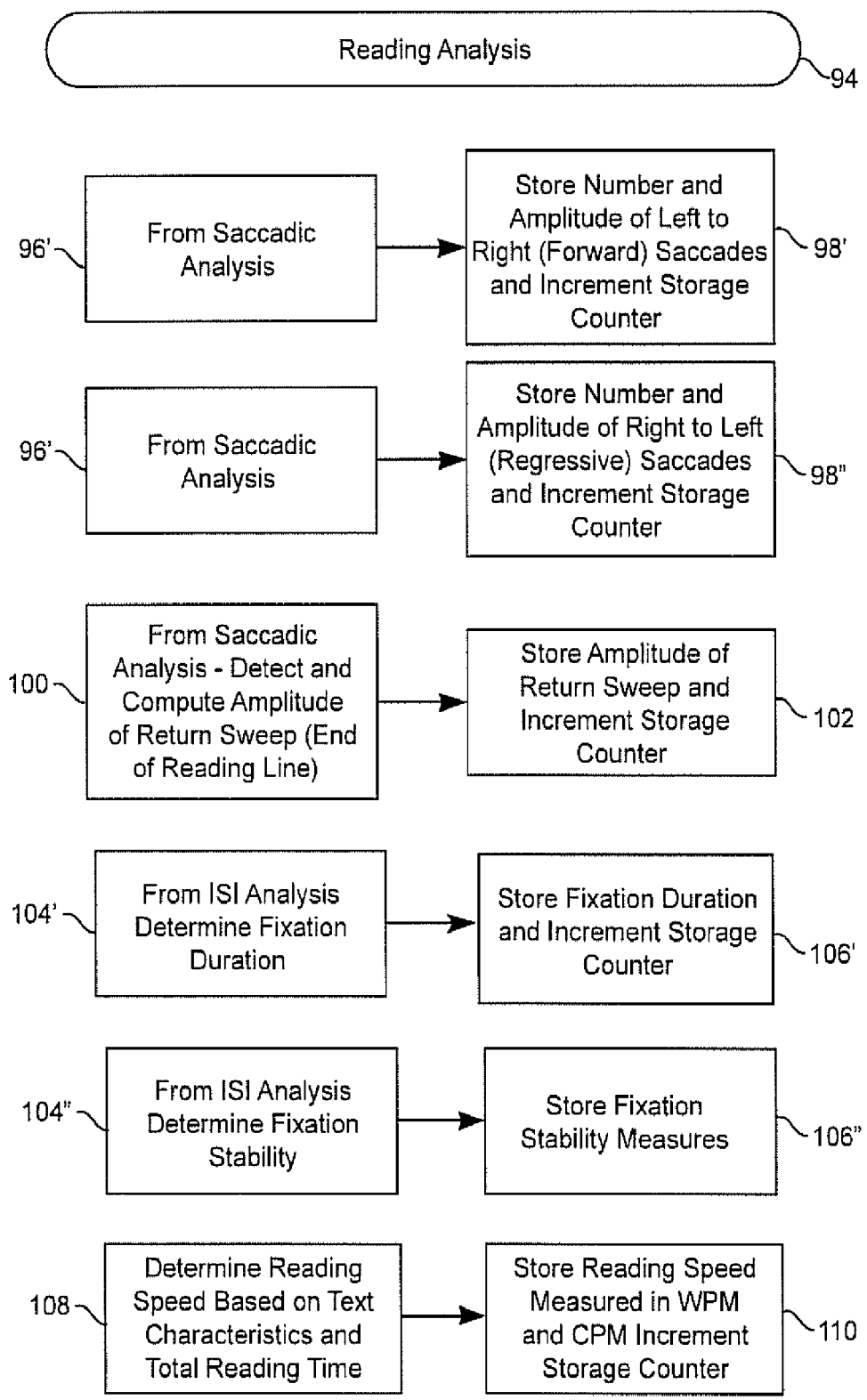
FIG. 5 is a schematic diagram illustrating an exemplary reading analysis subroutine of a saccadic analysis stage of FIG. 4.

FIG. 5 illustrates an exemplary reading analysis 94 in more detail. From the saccadic analysis 96' and 96" the number of left to right (forward) saccades 98' and the number of right to left (regressive) saccades 98" can be determined and stored using, for example, an increment storage counter. In addition, from the saccadic analysis 100, detection and computing of the amplitude of return sweep (end of reading line) can be determined and the amplitude of the return sweep can be stored 102 with, for example, incrementing of a storage counter. ISI analysis is discussed in more detail in connection with FIG. 6. In the context of the reading analysis of FIG. 5, from the ISI analysis, the fixation determination can be determined 104' and fixation stability can be determined 104", and each of these measures 106' and 106" (and/or other stability measures) can be stored, possibly with the updating of an increment storage counter. Furthermore, FIG. 5 shows that during reading analysis 94, the reading speed based on text characteristics and total reading time can be determined 108 and the reading speed, measured for example in word per minute (WPM) and/or characters per minute (CPM) can be stored 110, possibly with the incrementing of a storage counter.

Figure 6:
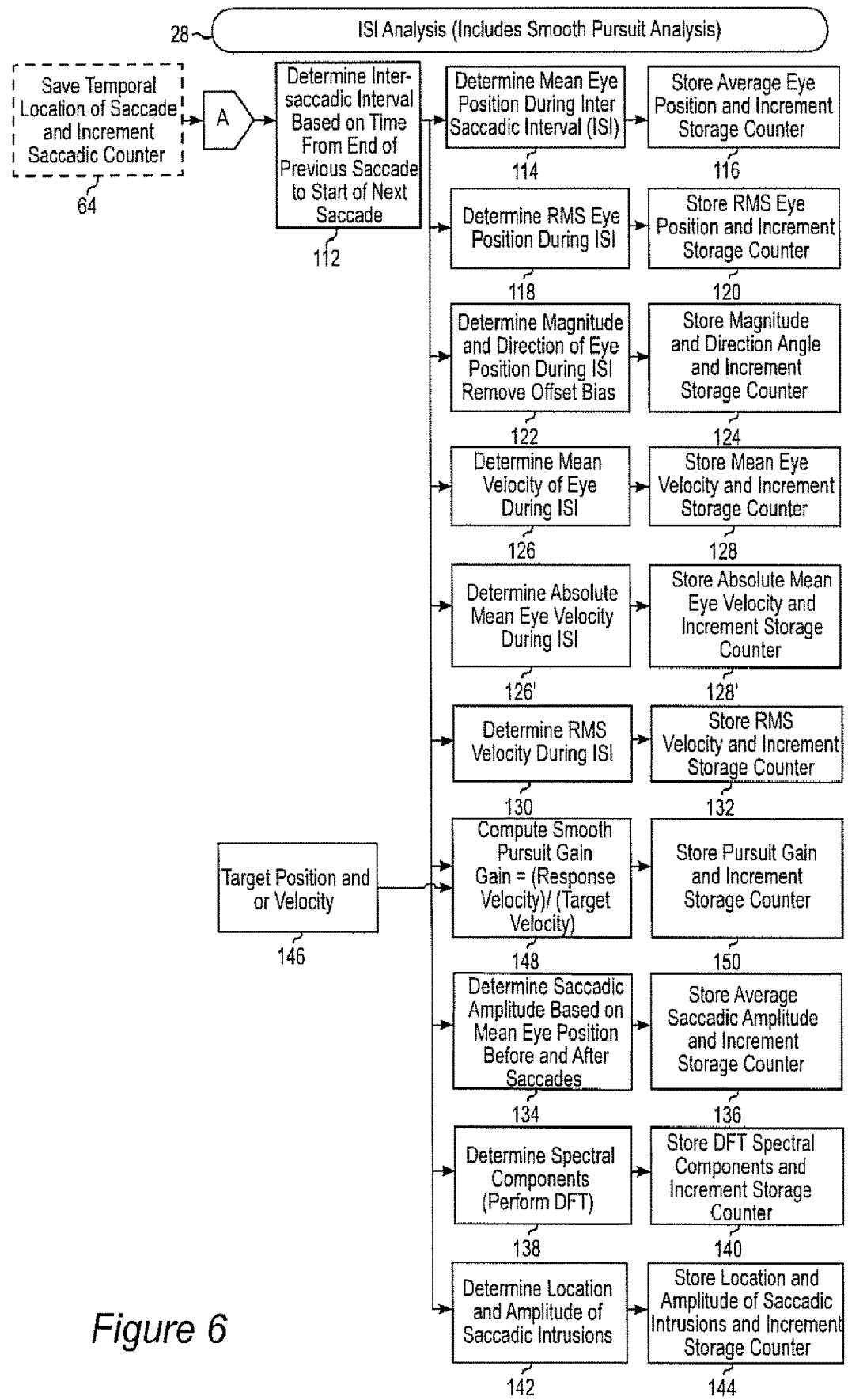
FIG. 6 is a schematic diagram illustrating an exemplary Intersaccadic Analysis Interval stage of FIG. 1.

FIG. 6 illustrates an intersaccadic interval (ISI) analysis stage 28. The intersaccadic interval defines the behavior or the eye during periods of fixation and or smooth pursuit eye movement. A number of neurological disorders often affect the stability of the eye during fixation in unique and specific ways. Calculations and assessment measurements of stability during fixation are performed and summarized within the ISI stage 28. Starting with data for the saved temporal location of saccade and incremented saccadic counter 64 from FIG. 3, the intersaccadic interval (ISI) is determined 112 based on the time from the end of the previous saccade to the start of the next saccade. From this, a number of different measures can be made including, for example and without limitation: a) the mean eye position during ISI can be determined 114 and stored 116 with, in some instances, the advancement of an increment storage counter; b) the Root Mean Square (RMS) eye position during ISI can be determined 118 and stored 120 with, in some instances, the advancement of an increment storage counter; and c) the magnitude and direction of eye position during ISI can be determined 122. The offset bias may also be removed. The magnitude and direction angle can be stored 124 with, in some instances, advancement of an increment storage counter. In addition, d) the mean eye velocity during ISI 126 and absolute mean eye velocity during ISI 126' can be determined and stored 128 and 128' with, in some instances, the advancement of increment storage counter; e) the RMS velocity during ISI can be determined 130 and stored 132 with, in some instances, advancement of an increment storage counter; f) the saccadic amplitude based on mean eye position before and after saccades can be determined 134 and the average saccadic amplitude can be stored 136 with, in some instances, the advancement of an increment storage counter; g) the spectral components can be determined 138 (this can be done by performing the Discrete Fourier transform (DFT) and stored 140 with, in some instances, advancement of an increment storage counter; and h) the location and amplitude of saccadic intrusions can be determined 142 and stored with, in some instances, advancement of an increment storage counter. Based on the target position and/or velocity 146 (as can be determined from the preprocessing of X or Y position 36, and computation of eye velocity 44), the ISI interval can be used to compute smooth pursuit gain 148 (where the gain equals the response velocity divided by the target velocity) and this value can be stored 150 with, in some instances, advancement of an increment storage counter.

With reference back to FIG. 1, the results from various analysis algorithms are presented to a decision matrix stage 14. Data for various groups of subjects are collected and categorized. For example, one may have a control group, as well as groups of patients with one or more neurological disorders including without limitation Parkinson's Disease (PD), Essential Tremor (ET), subjects with both PD and ET, small vessel ischemia, Multiple System Atrophy (MSA), Progressive Supranuclear Palsy (PSP), Corticobasal Ganglionic Degeneration (CBGD), drug induced tremor, Normal Pressure Hydrocephalus (NPH), and malingering. For example, Table 1 presents in various rows of specific eye movement parameters and their association for various neurological conditions. By comparing a subject's measurements with, for example, the unique combinations of abnormal eye movements can be used to provide a diagnosis (before or after a patient is symptomatic for the disease, disorder or injury) or to confirm a diagnosis or to monitor a treatment regimen after diagnosis and treatment has begun (e.g., improvements being when the responses of the subject become more normal with time and treatment (i.e., more like those of a normal subject and less like a subject with a particular neurological disease, disorder or injury) and non-improvements being either a lack of change with treatment or a decline (i.e., more like those of a subject with the diagnosed disorder or disease or injury). With respect to Table 1, the types of saccadic parameters determined to be generally of interest include peak velocity (e.g., whether or not the peak velocity is speeded up or slowed down relative the peak velocity for normal subjects, and, if so, by how much), latency (whether or not the latency (response to movement of the light source) is similar to normal subjects or slowed down (and if slowed down, by how much), and saccadic measurements (e.g., whether or not there is a hypometric saccadic refixation (e.g., a slowed response or undershoot) or hypermetric saccadic refixation (e.g., overshooting of the target). In the practice of the invention, one or a plurality of saccadic measurements for a subject are determined and automatically compared with stored saccadic measurements for normal subjects and for control subjects with diagnosed neurological diseases, disorders or conditions. In addition, in the practice of the invention typically a fixation measurement (e.g., ocular tremor) or a measurements associated with interruptions (e.g., increases or changes in square wave jerks) are also considered. Table 1 also includes a number of fixation type measurements and measurements associated with interruptions which have been considered, and which may be included in an automated computer implemented method or system.

TABLE 1

DECISION MATRIX AND LIKELY DIAGNOSIS STAGE

| | Normal Controls | Parkinson's Disease | Essential Tremor | PD + ET | Small vessel ischemia | MSA | PSP | CBGD | Drug-induced tremor | NPH | Malingering |
|---|---|---|---|---|---|---|---|---|---|---|---|
| Saccades (reflexive unless noted): | | | | | | | | | | | |
| Normal Peak Velocity (as determined by controls) | x | x | | | | | | x | x | | x |
| Slowed Peak Velocity (>20% slower than control) | | | x | | x | x | | x | | x | |
| Severely Slowed Peak Velocities (>50% slower than controls) | | | | | | | x | | | | |
| Slowed vertical velocities (esp. downward) (>20% slower than controls) | | | | | | x | x | | | x | |
| Increased Peak Velocities (>15% faster than controls | | | | x | x | | | | | | |
| Increased variability of peak velocities (Standard deviation >50% of controls) | | | | | x | | | | | | |
| Increased Q-ratio (peak vel/avg vel) (values >25% above control Avg) | | | x | | | | x | | | | |
| Normal latencies (determined by controls) | x | x | | | | x | | x | | | x |
| Slightly increased latencies (15% longer than controls) | | | x | x | | x | | | x | | |
| Severely increased latencies (30% longer than controls) | | | | | | | x | | | x | |
| Normal Metrics (as determined by controls) | x | x | x | x | | | | | x | | x |
| Hypometric to target movement | | | | | x | x | x | | | x | |
| Hypermetric to target movement | | | | x | | | | | | | |
| Dysmetric (mixed) | | | | | | | | x | | x | |
| Lack of saccadic prediction for temporally guided saccades | | x | | x | x | x | x | | | x | |
| Paucity (or reduced amplitude) of self guided, intrinsic saccades | | x | | | | x | x | | | x | |
| Vertical ripple during horizontal saccades (ie. "neural cross talk") | | | | | x | | | | | | |
| Unilateral saccade deficits (diffenent problems moveing R vs. L) | | | | | | | | x | | | |
| Fixation: | | | | | | | | | | | |
| Normal, stable fixations (determined by controls) | x | | x | | | | x | | | | x |
| Pervasive Ocular Tremor (single, consistent frequency, rhythmic) | | x | | x | | | | | | | |
| Complex fixation instability (chaotic, multiple or shifting frequencies) | | | | | | x | | | | | |
| High frequency, fine amplitude chaotic tremor | | | | | | | | | x | | |
| Chaotic fixations, random and non-rhythmic | | | | | x | x | | x | | x | |
| Poor vertical control | | | | | | x | | | | x | |
| Drift during fixation | | | | | x | | x | x | | x | |
| Interuptions: | | | | | | | | | | | |
| Increased (frequency of square wave jerks) (>10/min) | | | x | x | | x | x | | | | |
| Single pulse saccadic intrusions | | | | | x | x | | x | | x | |
| double pulse saccadic intrusions | | | | x | x | x | | | | x | |
| Macro-saccadic oscillations | | | | | | | | x | | | |
| Increased blink rate (>15% of controls) | | | | | x | | | | | | |
| Other: | | | | | | | | | | | |
| Smooth Pursuit gain >1 | | | | | | x | | | | | |
| Does not move in response to target, wandering gase | | | | | | x | x | | | | |
| Non-cooperative, makes volitional movements to prevent recording | | | | | | | | | | | x |

The Decision Matrix Stage 14 can be trained with or loaded with data from any group of patients with a distinctive, diagnosed, neurological disorder. With this information in the decision matrix, a subject can be tested, quickly, and non-invasively, and typically by untrained personnel. In particular, once the subject looks into a monocular or binocular window, the system will present moving lights and other stimuli with the eye movements of the subject being simultaneously monitored. At the conclusion of the test, the subject will be identified as either having a normal response (e.g., responses similar to a normal control group) or having a response similar to one or more groups of subjects which have neurological disorders. Based on these results, additional tests might be performed and/or therapy might be prescribed for addressing the identified disorder.

Figure 7A:
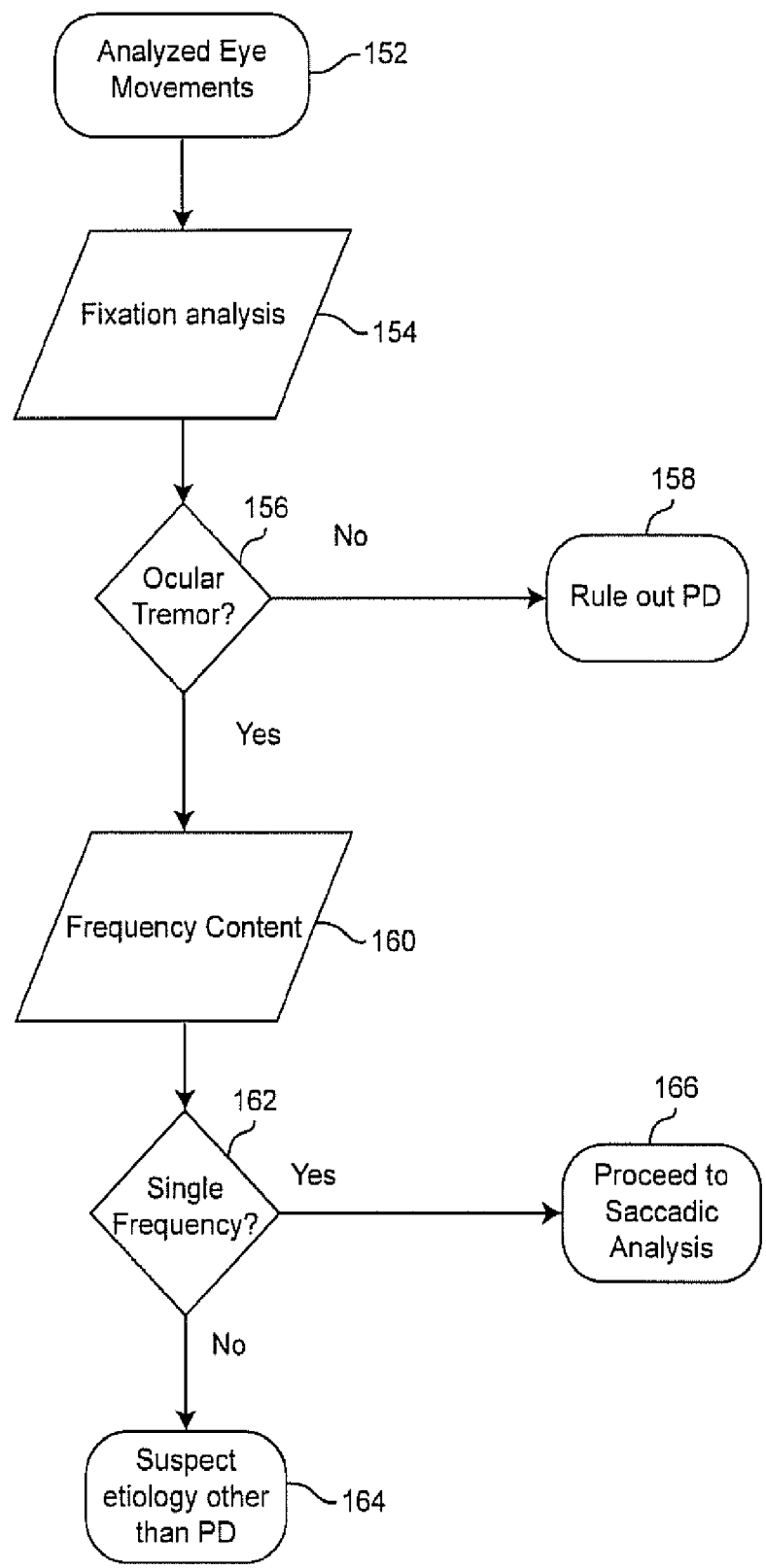
FIGS. 7A-B are flow charts showing a simplified system and process for diagnosing or confirming the diagnosis of Parkinson's disease.
Figure 7B:
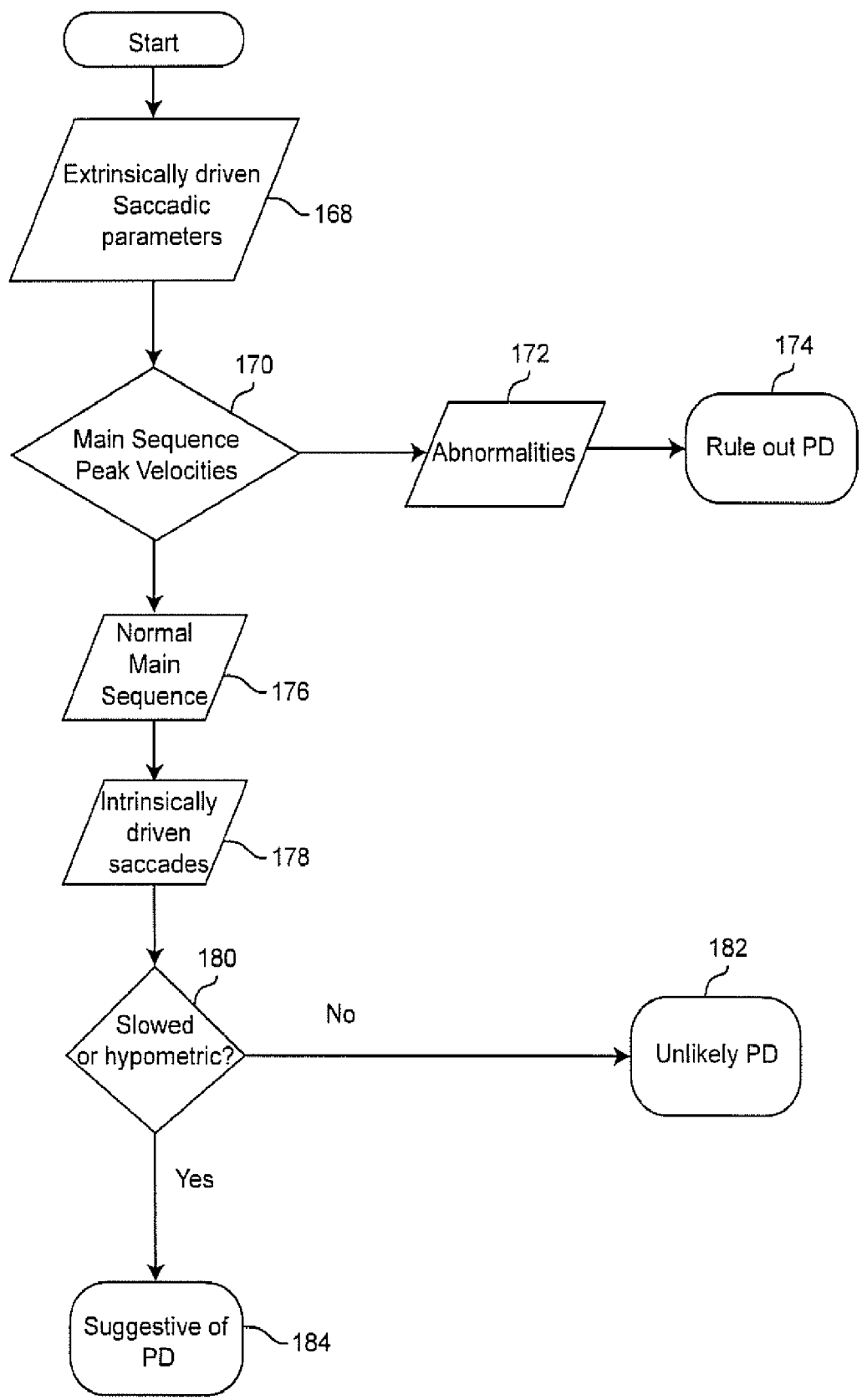

FIGS. 7A-B illustrates a simplified system and method for assessing Parkinson's Disease (PD) using an embodiment of the invention. Based on analyzed eye movements 152 determined using the eye tracker and algorithm stage, fixation analysis 154 is performed during the ISI analysis 28. If an ocular tremor 156 is detected, the subject is unlikely to have PD 158. Based on frequency content 160 as determined during the spectral component determination 136, a determination of a single frequency 162 (i.e. one frequency determined during DFT 136, as opposed to numerous spectral frequency components) and if more than one single frequency exists the subject is likely to have an etiology that is not PD 164. However, if single frequency does exist, the testing proceeds to saccadic analysis 166. It should be recognized that in cases where the diagnosis of a subject from amongst a number of possible neurological disorders or injuries, one would proceed to saccadic analysis as a matter of course, and one would use a decision matrix table (preferably in computerized form) similar to Table 1 to identify the disorder or injury. With reference to FIG. 7B, the extrinsically driven saccadic parameters 168 as calculated during saccadic analysis 26, have their main sequence peak velocities reviewed 170, and if there are abnormalities (compared to normals) 172, Parkinson's is unlikely 174. When a normal main sequence 176 exists, the intrinsically driven saccades 178 are analyzed to see if they are slowed or hypometric (e.g., undershoot of the target). If not, Parkinson's is unlikely 182, but if so, the results are suggestive of Parkinson's.

Figure 8A:
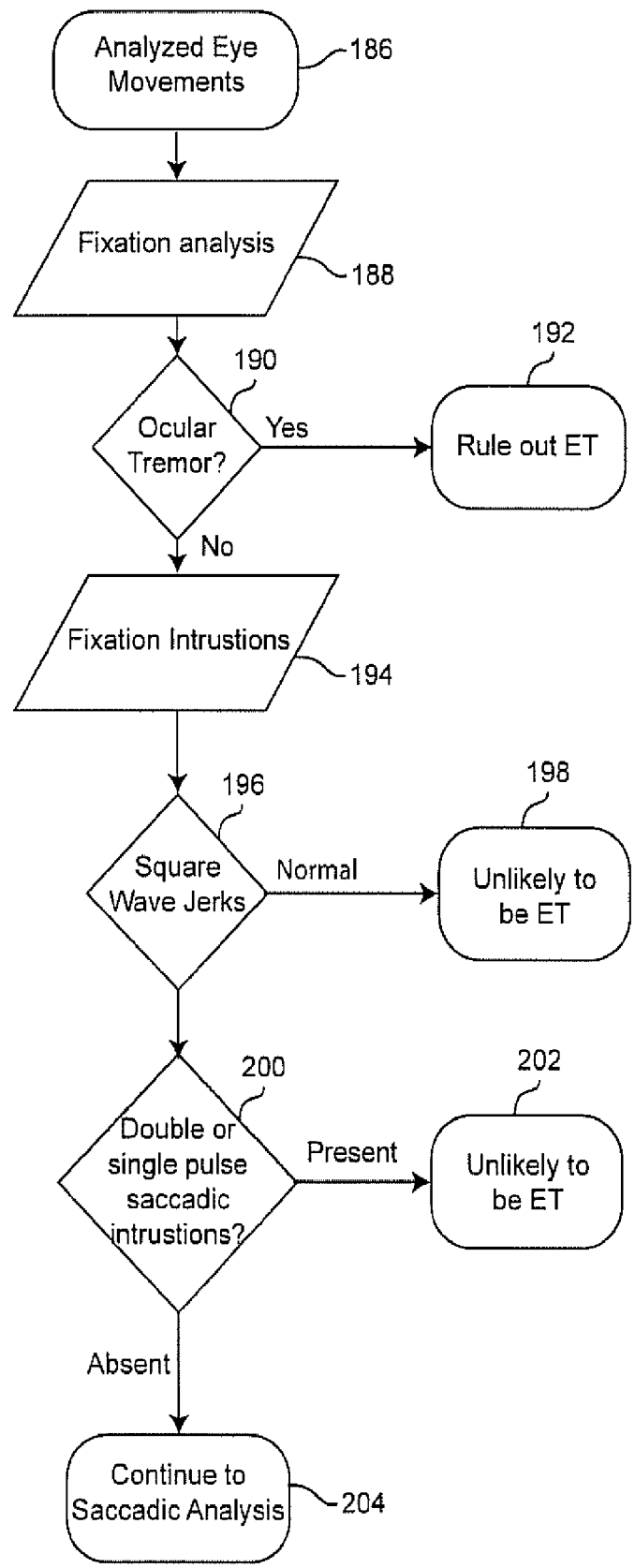
FIGS. 8A-B are flow charts showing a simplified system and process for diagnosing or confirming the diagnosis of Essential Tremor.
Figure 8B:
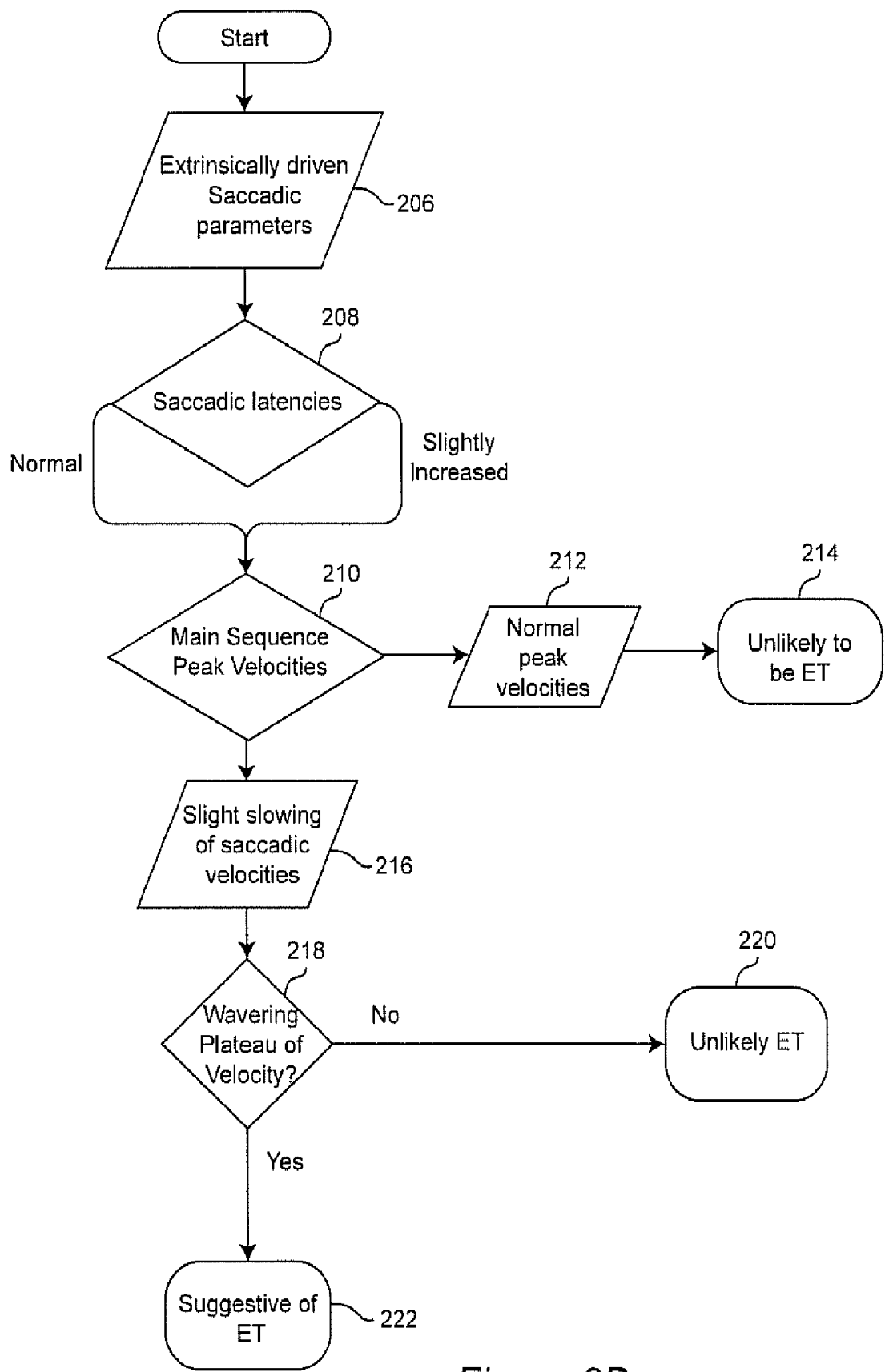

FIGS. 8A-B illustrate a simplified system and method for assessing Essential Tremor using an embodiment of the invention. Based on analyzed eye movement 186 determined using the eye tracker and algorithm stage, fixation analysis is performed and, if ocular tremor 190 is found, essential tremor can be ruled out 192 as a neurological disorder for the subject under test. Fixation intrusions 194, or interruption of intended fixation by saccades, drifts, etc, are analyzed for square wave jerks 196 (conjugate, brief, binocular to-and-fro movements of the eyes that interrupt steady fixation) and if they are normal, the subject is unlikely to be suffering from Essential Tremor 198. Double or single pulse saccadic intrusions are analyzed 200 and, if present, the subject likely does not have Essential Tremor 202. During saccadic analysis 204, extrinsically driven saccadic parameters 206 as calculated during saccadic analysis 26 are analyzed for saccadic latencies 208 (time from target movement to subject reaction) The main sequence peak velocities 210, and if normal 212, the subject likely does not have Essential Tremor 214. If there is a slight slowing of saccadic velocities 216, it is determined whether there is a wavering plateau of velocity 218 (as compared to a single peak of velocity in controls and other disorder). If not, then the patient does not likely have Essential Tremor 220. However, if so, then the patient, the existence of the results is suggestive of Essential Tremor 222.

It will be readily apparent to one of ordinary skill in the art that the various processes described herein may be implemented by, e.g., appropriately programmed general purpose computers, special purpose computers and computing devices. Typically a processor (e.g., one or more microprocessors, one or more microcontrollers, one or more digital signal processors) will receive instructions (e.g., from a memory or like device), and execute those instructions, thereby performing one or more processes defined by those instructions. Instructions may be embodied in, e.g., one or more computer programs, one or more scripts.

Within this application, the term "processor" or "computer" means one or more microprocessors, central processing units (CPUs), computing devices (e.g. desk top computer, lap top computers, tablets, personal data assistants, smart phones, dongles, etc.), microcontrollers, digital signal processors, or like devices or any combination thereof, regardless of the architecture (e.g., chip-level multiprocessing/multi-core, RISC, CISC, Microprocessor without Interlocked Pipeline Stages, pipelining configuration, simultaneous multithreading). The system and method of this invention may be implemented on a single computer 12', a network of computers 12', or by cloud computing across one or multiple networks 12' whereby the systems and networks can deliver the software which implements the system and method as a service.

Similarly, a description of a process is likewise a description of an apparatus for performing the process. The apparatus that performs the process can include, e.g., a processor and those input devices and output devices 14' that are appropriate to perform the process. Programs that implement such methods (as well as other types of data) may be stored and transmitted using a variety of media (e.g., computer readable media) in a number of manners. In some embodiments, hard-wired circuitry or custom hardware may be used in place of, or in combination with, some or all of the software instructions that can implement the processes of various embodiments. Thus, various combinations of hardware and software may be used instead of software only.

The term "computer-readable medium" refers to any medium, a plurality of the same, or a combination of different media, that participate in providing data (e.g., instructions, data structures) which may be read by a computer, a processor or a like device. Such a medium may take many forms, including but not limited to, non-volatile media, volatile media, and transmission media. Non-volatile media include, for example, optical or magnetic disks and other persistent memory. Volatile media include dynamic random access memory (DRAM), which typically constitutes the main memory. Transmission media include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave as described hereinafter, or any other non-transient computer readable medium from which a computer can read. Various forms of computer readable media may be involved in carrying data (e.g. sequences of instructions) to a processor. For example, data may be (i) delivered from RAM to a processor; (ii) carried over a wireless transmission medium; (iii) formatted and/or transmitted according to numerous formats, standards or protocols, such as Ethernet (or IEEE 802.3), SAP, ATP, Bluetooth, and TCP/IP, TDMA, CDMA, and 3G/4G/LTE; and/or (iv) encrypted to ensure privacy or prevent fraud in any of a variety of ways well known in the art.

Output from the automated system and method may be provided to an output device 14' which can take any form suitable for its intended purpose, and be provided to a printer, a display, a computer or network of computers, and may provide visual or audible signals which can be discerned by a clinician or researcher. The computer(s) or network of computers 12' used for processing information from the eye tracker may be directly or remotely connected to the eye tracker and may be in communication (wireless or wired) over a network such as the Internet. The stored values or ranges of values for normal subjects and control subjects diagnosed with a particular neurological disease, disorder or injury may be on a database (e.g., a non-transient computer readable medium) that is on or accessible to a single computer or may be stored separately on different computers within a network. In one embodiment, a subject looks into an eye tracker configured to provide fixed and moving light stimuli which will elicit detected responses that can be used by a computer or network of computers 12' to identify one or more values for one or more saccadic measurements and one or more values for fixation measurements or measurements associated with interruption. Upon providing the detected responses to the computer or network of computers, the responses are automatically analyzed and characterized, and various values for, for example, one or more saccadic measurements and one or more fixation measurements or measurements associated with interruption, are compared to stored values or ranges of values associated with responses of normal subjects or responses of control subjects which have been diagnosed with a neurological disorder, disease or injury. Matches from this comparison are output to the clinician or researcher, preferably on an automated basis. The testing may take place on the order of seconds (depending on the number of measurements desired), and the determinations, comparisons and output may take place on the order of seconds to minutes depending on the number of values to be computed and compared and the number of different stored values or value ranges to be considered.

Example 1

Pervasive Ocular Tremor in Patients with Parkinson Disease

Objective:

Ocular motility deficits have been well characterized in Parkinson's Disease (PD) patients. However, abnormalities of fixation stability have only been briefly reported and never systematically quantified in PD subjects. The aim of this study was to assess oculomotor control of patients with PD during fixation and with movement. Design: Modern, precise eye tracking technology was used to assess oculomotor parameters in 112 patients with PD, including 18 de novo untreated patients, and 60 age matched controls. Oculomotor function was compared between groups during fixation and while tracking a randomly displaced target on a PC monitor. Results: All PD patients, and 2 out of 60 control subjects, showed oscillatory fixation instability (ocular tremor), with an average fundamental frequency of 5.7 Hz and average magnitude of 0.27°. Saccadic parameters and occurrences of square wave jerks did not differ between PD subjects and controls. The amplitude and frequency of fixation instability did not correlate with disease duration, clinical Unified Parkinson's Disease Rating Scale (UPDRS) scores, or dopa-equivalent dosing. No differences in oculomotor parameters were found between medicated and unmedicated PD patients. Conclusions: All PD patients exhibited persistent ocular tremor which prevented stability during fixation. The pervasiveness and specificity of this feature indicates that modern, precise oculomotor testing can provide a valuable early physiological biomarker for diagnosing PD.

Introduction

Previous studies in patients with Parkinson's disease (PD) have shown that the neurodegenerative changes in the brain affect the oculomotor control system, as it does the appendicular motor control.[1,2,3] Although a number of studies describe various oculomotor abnormalities in PD subjects, conflicts about the specific deficits remain. Some investigators have suggested that the principle abnormalities are reduced velocity and increased duration of saccades,[4,5,6,7,8] while others have suggested that the frequency of square wave jerks (brief, conjugate, random movements away from the target that interrupt stable fixations) are increased.[8,9] Deficits in ocular fixation, during which we critically fixate on objects to acquire information about the world around us, have been subjectively described in PD, but have not been systematically quantified.[10,11] In the present study, we utilized modern eye tracking equipment to investigate oculomotor control in PD subjects while fixating and during saccades to a randomly step displaced target.

Methods:

For this study, 112 patients with PD (mean age: 66.2, S.D.±6.8) and 60 age matched controls (mean: 65.3, S.D.±7.4) were recruited from the Southeast Parkinson's Disease Research, Education and Clinical Center (PADRECC) at the Richmond Veteran's Affairs Medical Center. All patients were screened by a movement disorder specialist (M.S.B.) and considered to have PD based upon the criteria of having at least two of three cardinal signs (i.e. rest tremor, rigidity, and akinesia/bradykinesia), without features suggestive of secondary forms of parkinsonism. 94 of the patients had shown a clear therapeutic benefit to dopaminergic medications, and 18 patients were de novo untreated. The average duration of symptoms was 5.5 years (S.D.±4,3) with a mean Unified Parkinson's Disease Rating Scale (UPDRS) part III examination score of 12.1 (S.D.±9.6). The average tremor susbscore of the UPDRS was 2.2 (S.D.±1.4). All medicated patients were tested while taking their normally prescribed medications, with an average dopa-equivalent[12] of 872.3 (S.D.±510.1). Patients with superimposed neurological or ophthalmic conditions (e.g. glaucoma, macular degeneration, etc.) were excluded. Control subjects were recruited among spouses, relatives, and friends and were screened and similarly excluded if they had any significant neurological or ophthalmic conditions. See Table 2 for a summary of study subject characteristics.

TABLE 2

Subject Enrollment

| | Medicated PD (n = 94) | Unmedicated PD (n = 18) | Controls (n = 60) |
|---|---|---|---|
| Age (years) | 62.6 ± 11.2 | 65.8 ± 13.5 | 65.3 ± 7.4 |
| Duration of symptoms (years) | 6.1 ± 4.0 | 1.4 ± 0.9 | — |
| UPDRS Part III Examination | 17.1 ± 7.2$^a$ | 17.9 ± 4.8 | — |
| UPDRS tremor subscore | 2.4 ± 1.4$^a$ | 1.8 ± 1.4 | — |
| Levodopa only | n = 77 | — | — |
| Levodopa + entacapone | n = 2 | — | — |
| Levodopa + ropinerole | n = 8 | — | — |

TABLE 2-continued

Subject Enrollment

|  | Medicated PD (n = 94) | Unmedicated PD (n = 18) | Controls (n = 60) |
|---|---|---|---|
| Levodopa + amantadine | n = 7 | — | — |
| RMS Velocity (during fixation) | 5.32 ± 2.14* | 4.63 ± 1.11* | 3.18 ± 0.46 |

[a]While tested in the "on" medicated state
*p < 0.001 compared to controls (with no significant differences between medicated and unmedicated PD subjects)

Both patients and controls were questioned as to whether they had any subjective visual complaints, such as blurred vision, double vision, or floaters. While subjects with ophthalmic conditions were excluded from the study; subjective visual complaints were not criteria for exclusion. The study was approved by the Institutional Review Board at the McGuire Veterans Affairs Hospital and written informed consent was obtained from all subjects prior to testing.

Using a video based binocular eye tracker (Eyelink II, SR Research Ltd, Ontario, Canada), horizontal and vertical gaze data were collected from each eye at 500 Hz. The system utilizes infrared lights and cameras placed just below each eye, beyond the field of vision, to track the center of the dark pupils. The system rests comfortably on the subjects head, allows free unrestricted head movement, is quick to setup and calibrate, and allows patients to wear their normal corrective prescription lenses. To exclude a potential contribution of head movements to the perceived ocular instability in PD subjects, head position was simultaneously recorded in 62 PD and 31 control subjects by means of a six degree of freedom magnetic tracking system (trakSTAR, Ascension Technology Corp., Shelburne, Vt.). The magnetic tracking system was set to sample at 125 Hz and was integrated and synchronized with the eye tracker. The spatial resolution of the trakSTAR system is 0.5 mm in terms of position, and 0.1° in terms of orientation.

Stimuli were presented in a darkened room on a 26" LCD monitor placed 75 cm from the subject's eyes, covering ±20° horizontally and ±13° vertically. For each subject, the height of the display was adjusted so that the center of the screen corresponded to the center of the pupillary plane. Calibration and validation of the eye tracker was performed on a nine point grid, immediately before recording commenced. Data were then collected while subjects followed approximately 100 random simple step changes in target position along the horizontal and vertical cardinal axes. The target stimulus was a white annulus sized to occupy 0.5° of visual angle, with a high contrast center point of 0.1° presented on a black background. Both the timing and amplitude of step displacements were random and unpredictable. Subjects were encouraged to close their eyes and rest between each recording to prevent fatigue.

Data were analyzed off line by a researcher blinded to the patient's diagnosis, using an interactive custom written plotting program (P.A.W). Fixations were analyzed for duration, number of square wave jerks, and stability. In cases of fixation instability, the data were subjected to a fast Fourier transform (FFT), and rhythmicity or tremor was assessed and a fundamental frequency was determined. To further quantify the fixation instability, the root mean square (RMS) of the velocity was computed during each fixation period. This measure accounts for the movement in all directions and permits quantification of the variability of the instability.

Saccades were analyzed for duration, peak velocity, acceleration, amplitude, and accuracy. Saccadic beginning and end points were determined by a velocity threshold set at 20°/sec, and saccadic velocity was calculated by way of a two point central difference. Additionally, the main sequence, a well established method originally described by Bahill and colleagues,[13] was used to examine the relationship between the amplitude of a saccade and its duration or peak velocity. In the occasional more extreme cases of fixation instability, saccadic start and end points were judged subjectively by the investigator.

All statistical analysis was conducted using SPSS Statistics 17.0. For statistical analyses, α was set to 0.05. Data was assessed for normality using the Shapiro-Wilk test. Parameters that were not normally distributed (i.e. Shapiro-Wilk p-value <0.05) were then log-transformed and confirmed to be log-normal distributions, and analyses were run on these values. Independent sample, unpaired, two-tailed I-tests were conducted to assess for differences between medicated, unmedicated, and control sample groups. Levene's test for the equality of variances was calculated, and if the significance was found to be less than 0.05, equal variances were not assumed. In the later instance, a Welch's t-test was used to compare the means, which has the ability to compensate for samples of unequal variance.

Results:
Fixation Stability:

While fixating on a target, all 112 PD patients showed persistent instability characterized by oscillatory behavior with a mean fundamental frequency of 5.7 Hz (S.D.±1.5 Hz), ranging from 4.3 to 10.9 Hz. In contrast, 58 of the 60 control subjects (96.6%) showed highly stable fixations characterized by minimal drift of gaze and no oscillatory behavior. Two control subjects (3.3%) exhibited oscillatory fixation instability similar to that in PD subjects. The mean amplitude of the fixation instability in PD subjects was 0.27° (S.D.±0.25°) horizontally and 0.33° (S.D.±0.28°) vertically, ranging from 0.14° to 1.63°. The vertical component of the instability was of greater magnitude than the horizontal component in 92 of the 112 subjects (82.1%). In 71 subjects (63.3%), the maximum amplitude of the instability at times reached the 0.5° estimated threshold for obscuring foveal vision.[1] The amplitude of instability regularly fluctuated and was not influenced by the gaze angle. In contrast to the amplitude, the fundamental frequency for each subject never varied by more than 1 Hz. All oscillatory eye movements were conjugate in nature, with the phase locked in both eyes. Additionally, the phase of the ocular tremor remained stable over the recordings, not resetting or shifting with saccades, blinks, or other eye movements. Magnetic head tracking in a subset of patients affirmed that head movements did not contribute to the ocular instability findings. Small, brief periods of translational head movements were observed when a patient shifted in the chair, but no tremulous head activity was found in any of the tested patients.

Figure 9A:
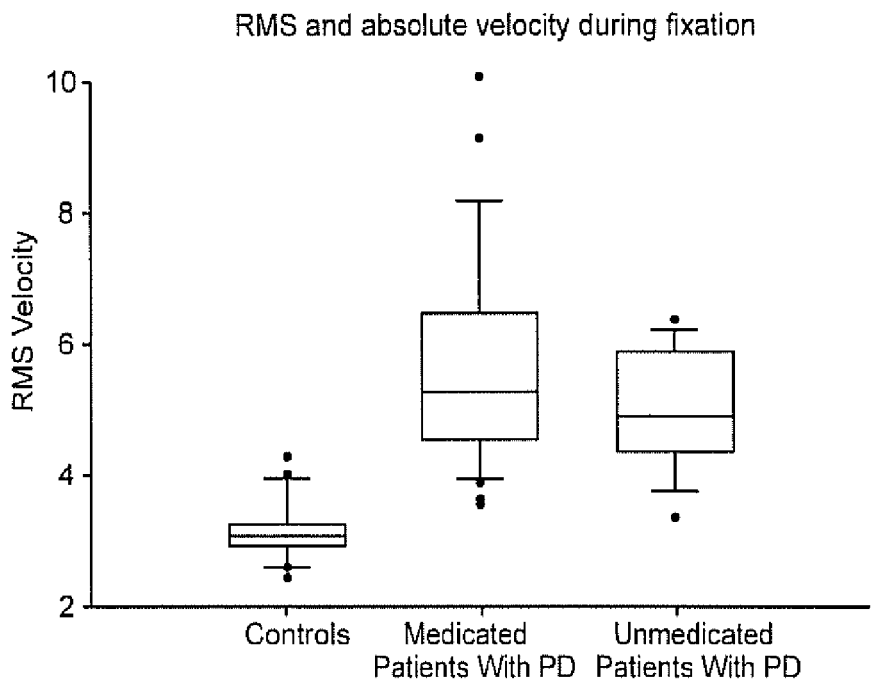
FIGS. 9A-B: Root mean square (RMS) velocity and absolute velocity during fixation for control and PD groups. Oscillatory fixation instability in PD patients results in a greater RMS velocity (A) and absolute velocity (B) of the eye during fixation. Middle bars inside boxes represent sample means, while the edges of boxes indicate first and third quartiles. Bottom and top bars represent minimum and maximum, respectively. Circles denote outliers, while an asterisk denotes an extreme outlier.
Figure 9B:
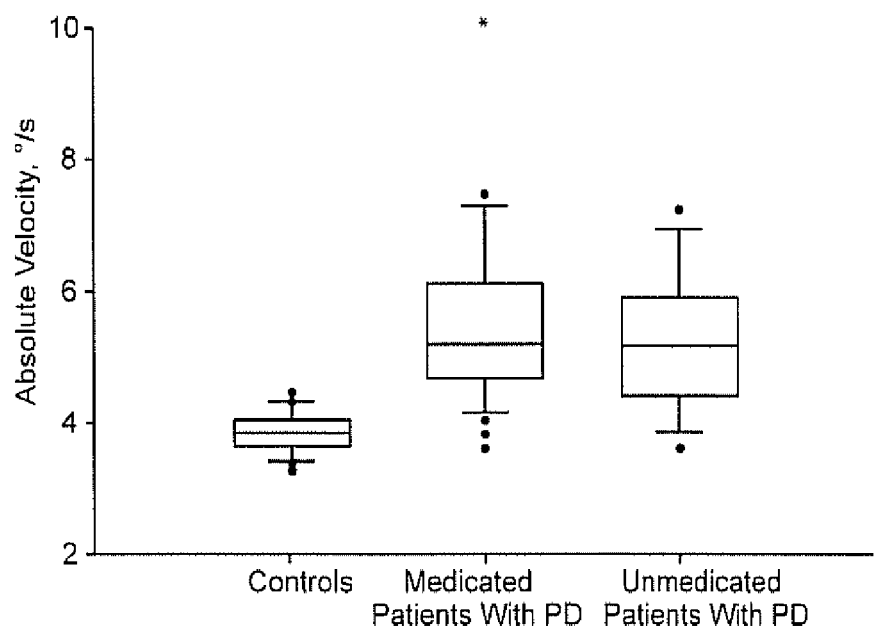

As a measure of the fixation instability, the mean RMS velocity during fixation was 5.72°/s (S.D.±3.01) in the PD group compared to 3.07°/s (S.D.±0.41) in the control group (p<0.0001, FIG. 9A). The absolute average velocity was 3.11°/s (S.D.±0.26) in the PD group compared to 1.80°/s (S.D.±0.25) in the control group (p<0.001, FIG. 9B). Comparisons between groups for RMS velocity and absolute velocity of each eye measured separately,[14] in both the horizontal and vertical direction, as well as the standard deviation of velocity of both eyes in each direction all reached significance (each at p<0.0001). As another means of displaying the magnitude of the ocular instability[15], From a two dimensional plot of fixation points at the origin (not shown) there was a comparatively much larger range of movements and variability during fixation in the medicated PD group. None of the measured fixation parameters correlated with UPDRS part III examination scores, tremor subscores, or disease duration. Additionally, there were no differences found between medicated versus non-medicated patients in terms of fundamental frequency (p=0.822), magnitude (p=0.551), or RMS velocity (p=0.714) of ocular tremor. The number of square wave jerks did not differ between PD (11.2/min, S.D.±9.4) and control (12.6/min, S.D.±8.5) groups (p=0.587).

Saccadic Parameters:

Saccadic latency to step displaced random targets did not differ between the PD (237.4 ms, S.D.±39.8) and control (232.5 ms, S.D.±33.2) groups (p=0.776). Saccadic amplitude, velocity, and duration also did not differ between PD and control groups. For each group, similar exponent values were found for the main sequence duration equation (n for PD=0.31, controls=0.33), and for peak velocity (C for PD=11.2, controls=12.6). In each group, the main sequence equations showed a comparable exponential rise to a maximum value. Also, for both groups, the product of saccadic duration and peak velocity showed a comparable linear relationship. Data on over 14,000 saccades of controls and medicated PD subjects showed no statistical difference of the slope of regression lines for peak velocity times duration versus amplitude between the two groups (Z=0.554).[16]

Discussion

The major finding of the present study was that using modern eye movement tracking, we demonstrated oscillatory fixation instability in all 112 tested patients with PD. Although fixation instability had been subjectively described in other studies,[10,11] its pervasiveness had not been previously recognized nor had it been systematically quantified. Duval and Beuter[11] previously described findings of ocular tremor in PD, which did not correlate with appendicular rest tremor. However, the authors limited their investigation to 5 cases and did not study the ocular tremor in detail. Further, they reported monocular oscillations in 2 of the subjects, which we never observed in our large cohort. To the best of our knowledge, our study is the first to thoroughly describe fixation instability in a large cohort of PD patients. In difference to our study, prior investigators chiefly focused on the disruption of fixations by square wave jerks or saccadic intrusions in PD subjects, while reporting on the duration and mean displacement of the fixations.[17] The fact that this behavior was universally observed in every tested PD patient, including unmedicated patients, indicates that ocular tremor is a function of the disease process and not induced by medication. The lack of head instability in the subset of patients undergoing head monitoring affirms that perceived ocular instability is not attributable to head related movements, nor is it compensatory in nature.

The fixation instability in PD to an extent resembles that of pendular nystagmus, but with notable differences. Although the fundamental frequency of the waveform and the consistency of the fundamental frequency in each patient are consistent with that of pendular nystagmus[18], the complexity and smaller magnitude of the waveforms in PD differ substantially from that generally characteristic of pendular nystagmus. Pendular nystagmus is most typically purely sinusoidal, whereas the instability in PD appears more chaotic with multiple sinusoidal frequency components. The amplitude of the waveform in pendular nystagmus is typically an order of magnitude larger than that in PD. Additionally, while the oscillations in pendular nystagmus are produced by a neural integrator which resets the phase with saccades[19], the phase of the oscillations in PD is not reset by a saccade. Largely on these bases, we feel that the oscillations in PD do not represent pendular nystagmus and instead we have determined that "ocular tremor" appropriately exemplifies the fixation instability in PD. Moreover, pendular nystagmus is typically associated with disorders of central myelin[18], spinocerebellar degeneration[20], and visual loss[21], none of which are associated with PD. Future studies will be required to determine whether the ocular and appendicular tremors in PD originate from similar or different pathological loci.

Among 60 control subjects, 58 (96.6%) showed very stable fixations. The two controls with abnormal fixations, corresponding with the two outliers in the RMS velocity box plot, exhibited oscillatory fixation instability indistinguishable from that in patients with PD. When their eye movements were initially recorded, neither of the two subjects noted parkinsonian symptoms or showed objective parkinsonian signs. However, both subjects have been followed at least yearly and one began to manifest parkinsonian features, including unilateral rest tremor and abnormal finger tapping, at the two year follow-up examination.

In contradiction to prior reports,[8,9] patients showed no differences in frequency of square wave jerks compared to control subjects. Although Rascol and colleagues[9] suggested that 15% of their patients showed an increased frequency, their criteria of 10 square wave jerks per minute approximates the mean occurrence observed in both our control and PD subjects. Hikosaka and Wurtz demonstrated changes in the firing pattern of the Substantia Nigra pars *Reticulata* in response to internally driven, self paced saccades versus externally driven reactionary saccades[22]. Presently, all measured saccadic parameters, including latency, peak velocity, duration, and accuracy did not differ between PD subjects and controls for saccades made in response to randomly step displaced targets. Additionally, saccadic measures were equivalent between the treated and untreated patient groups. Although we would expect to see saccadic abnormalities in self paced or memory guided saccades in PD[4,7,9,23,24], we did not expect to see differences in reflexive, externally driven saccades[5,21,22,25]. Our data is consistent with these findings previously described by others.[26,27]

We have established that fixation instability is a pervasive feature in patients with PD. During fixations, the eyes of PD patients constantly rhythmically move at an average frequency of 5.7 Hz, in small amplitude, complex oscillations. Because the fixation instability was present in all 112 tested patients (both medicated and de novo), and was evident in one apparently presymptomatic PD subject and in only one other control subject, precise oculomotor testing could serve as a valuable physiological biomarker for diagnosing PD at an early stage.

Acknowledgments:

The authors thank Abu Qutubuddin M.D. (Physiatrist, Southeast PADRECC, Hunter Holmes McGuire Veteran's Affairs Medical Center) and Peggy Roberge R.N. (Clinical Nurse Coordinator, Southeast PADRECC) for their assistance in recruiting study subjects.

REFERENCES

1. Ciuffreda K J, Tannen B. Eye movement basics for the clinician. St. Louis: Mosby; An Affiliate of Elsevier; 1995.

2. Leigh R J, Zee D S. The neurology of eye movements, Fourth Edition. New York: Oxford University Press, 2006.
3. Waterston J, Barnes G, Grealy M, Collins S. Abnormalities of smooth eye and head movement control in Parkinson's disease. Ann Neurol 1996; 39:749-760.
4. Rottach K, Riley D, DiScena A, Zivotofsky A, Leigh J. Dynamic properties of horizontal and vertical movements in Parkinsonian syndromes. Ann Neural 1996; 39:368-377.
5. Hikosaka O, Takikawa Y, Kawagoe R. Role of the basal ganglia in the control of purposive saccadic eye movements. Physiol Rev 2000; 80: 953-978.
6. Ramat S, Leigh R J, Zee D S. What clinical disorders tell us about the neural control of saccadic eye movements. Brain 2007; 130:10-35
7. Pinkhardt E H, Kassubek J. Ocular motor abnormalities in Parkinsonian syndromes. Parkinsonism Relat D 2011:17 (4); 223-230.
8. White O B, Saint-cyr J A, Tomlinson R D, Sharpe J A. Oculomotor deficits in Parkinson's disease. II. Control of the saccadic and smooth pursuit systems. Brain 1983:106; 571-587.
9. Rascol O, Sabatini U, Simonetta-Moreau M, et. al. Square wave jerks in Parkinsonian syndromes. J Neural Neurosurg Psychiatry 1991; 54:599-602.
10. Mallahan E L, Wetzel P A, Cifu D X, et. al. Visual impairments in Parkinson disease. Federal Practitioner 2006; 7:59-63.
11. Duval C, Beuter A. Fluctuations in tremor at rest and eye movements during ocular fixation in subjects with Parkinson's disease. Parkinsonism Relat D 1998; 4(2); 91-97.
12. Lang A, Lozano A, Montgomery E, et. al. Posteroventral medial pallidotomy in advanced Parkinson's disease. N Engl J Med 1997; 337:1036-1042.
13. Bahill A T, Clark M R, Stark L. The main sequence, a tool for studying human eye movements. Math Biosci 1975; 24: 194.
14 Kirkby J, Webster L, Blythe H, Liversedge S. Binocular coordination during reading and non-reading tasks. Psychol Bull 2008; 134:0033-2909.
15. Yarbus A L. Eye movements and vision. New York: Plenum. 1967.
16. Kleinbaum D G, Kupper L L. Applied regression analysis and other multivariate methods. $2^{nd}$ ed. Belmont: Wadsworth Publishing Company. 1978.
17. Pinnock R A, McGivern R C, Forbes R, Gibson J M. An exploration of ocular fixation in Parkinson's disease, multiple system atrophy, and progressive supranuclear palsy. J Neurol 2010; 257:533-539.
18. Averbuch-Heller L, Zivotofsky A Z, Das V E, Discenna A O, Leigh R J. Investigations of the pathogenesis of acquired pendular nystagmus. Brain 1995; 188: 369-378.
19. Das V E, Oruganti P, Kramer P D, Leigh R J. Experimental tests of a neural-network model for ocular oscillations caused by disease of central myelin. Exp Brain Res. 2000; 133(2):189-197.
20. Averbuch-Heller L, Tusa R J, Fuhry L, et, al. A double-blinded controlled study of gabapentin and baclofen as treatment for acquired nystagmus. Ann Neurol 1997; 41: 818-825.
21. Leigh R J, Thurston S E, Tomsak R L Grossman G E, Lanska D J. Effect of monocular visual loss upon stability of gaze. Invest Ophthalmol Vis Sci 1989; 30: 288-292.
22. Hikosaka O, Wurtz R H. Visual and oculomotor functions of monkey substantia nigra pars *reticulata*. III. memory-contingent visual and saccade responses. J. Neurophysiol. 1983; 49:1268-1284.
23. Shaunak S, O'Sullivan E, Blunt S, Lawden M, Crawford T, Henderson L, Kennard C. Remembered saccades with variable delay in Parkinson's disease. Mov Disord 1999; 14(1):80-86.
24. Lueck C J, Tanyeri S, Crawford T J, Henderson L, Kennard C. Saccadic eye movements in Parkinson's disease: 1. delayed saccades. Q J Exp Psychol A 1992; 45A(2):193-210.
25. Schrag A, Jahanshahi M, Quinn N. What contributes to quality of life in patients with Parkinson's disease? J Neurol Neurosurg Psychiatry 2000; 69:308-312.
26. Briand K A, Strallow D, Hening W, Poizner H, Sereno A B. Control of voluntary and reflexive saccades in Parkinson's disease. Exp Brain Res, 1999; 129(1): 38-48.
27. Armstrong I T, Chan F, Riopelle R J, Munoz D P. Control of saccades in Parkinson's disease. Brain Cogn. 2002: 49(2):198-201.

Example 2

Slowed Saccades and Increased Square Wave Jerks in Essential Tremor

Background

Eye movements in Essential Tremor (ET) are poorly described, and may present useful information on the underlying pathophysiology of the disorder.

Methods:

60 patients with ET, including 15 de novo untreated patients, and 60 age-matched controls comprised the study population. A video based eye tracker was used to assess binocular eye position. Oculomotor function was assessed while subjects followed random horizontally and vertically step-displaced targets.

Results:

For all reflexive saccades, latencies were increased in ET subjects by a mean of 16.3% (p<0.01). Saccades showed reduced peak velocities with a lengthy, wavering velocity plateau, followed by slowed decelerations. For larger 30°+ saccades, peak velocities were decreased by a mean of 25.2% (p<0.01) and durations increased by 31.8% (p<0.01). Patients showed more than triple the frequency of square wave jerks (SWJ's) compared to controls (p<0.0001). Despite frequent interruptions by SWJ's, fixations were otherwise stable and indistinguishable from controls (root mean square (RMS) velocity, p=0.324). The abnormal eye movement parameters were independent of disease duration, tremor severity, and medication therapy.

Discussion

In contrast to normally swift onset and efficient acceleration/deceleration movements, saccades in ET are characterized by abnormally prolonged latencies and slowed velocity profiles. Although ET subjects maintain highly stable fixations, they are interrupted by increased numbers of SWJ's. This study reveals novel oculomotor deficits in ET, which are distinct from the eye movement dysfunction of other movement disorders; and demonstrated that eye tracking can assist in the differential diagnoses of not only atypical, but also more common movement disorders.

Introduction

Essential Tremor (ET) affects approximately 4 percent of people over 40 years of age[1] and is commonly characterized by bilateral postural arm tremor, with or without tremor with action.[2] The tremor predominantly involves the hands and forearms, and less commonly affects the head or voice.[3] Even though ET is considered to be the most prevalent movement disorder,[4] the associated oculomotor deficits have not been well defined. In the only two published reports on eye movements in ET,[5,6] abnormalities were found in initiation of smooth pursuit and in suppressing vestibular nystagmus, deficits likely attributable to cerebellar dysfunction.[7,8,9] These groups also reported that saccades were unaffected; however, the analysis of the collected data suggested the need to more thoroughly investigate this relevant issue. Using comparatively more in depth and rigorous analyses of saccades, subjects in ET were found here to show distinct abnormalities in saccadic behavior. Moreover, the present study findings demonstrate novel oculomotor abnormalities in ET that are distinctly different from both controls and other movement disorders, such as Parkinson's disease (PD). Finally, the eye movement abnormalities lend support to the cerebellar pathophysiology of ET.

Methods

Sixty patients diagnosed with ET (age: 63.4 years±12.9, range: 26-88 sex: 48 (80%) males) and 60 similarly aged control subjects (65.3 years±7.4, sex: 40 (66.6%) male) completed oculomotor testing and comprised the study population. Patients were recruited consecutively from the Southeast/Richmond Veterans Affairs Medical Center Parkinson's Disease Research, Education and Clinical Center (PADRECC). All patients were screened by a movement disorder specialist (M.S.B.) and considered to have ET based upon the diagnostic criteria set forth by the consensus statement of the Movement Disorder Society.[2] Patients with deep brain stimulators or significant superimposed neurological or ophthalmic conditions were excluded. Control subjects were recruited among spouses, relatives, and friends and were screened and excluded if they had any significant neurological or ophthalmic conditions. The study was approved by the Institutional Review Board at the Hunter Holmes McGuire Veterans Affairs Hospital and written informed consent was obtained from all subjects prior to testing.

Among the 60 study patients, the average duration of tremor was 11.3 years (S.D.±13.7). To maintain consistency across other studies in our center, tremor severity was scored (0 to 4) according to the Unified Parkinson's Disease Rating Scale (UPDRS) Examination item 21, Action or Postural Tremor of Hands, and averaged 1.9 (±0.9). See Table 3 for a summary of subject enrollment.

TABLE 3

Subject Enrollment

| | Essential Tremor (n = 60) | Controls (n = 60) |
|---|---|---|
| Age (years) | 63.4 ± 12.9 | 65.3 ± 7.4 |
| Duration of symptoms (years) | 11.3 ± 13.7 | — |
| Gender: number of males (%) | n = 48 (80%) | n = 40 (66.6%) |
| Postural tremor score | 1.9 ± 0.9 | — |
| Square wave jerks per minute | 26.9 ± 20.0* | 8.4 ± 8.3 |
| Saccadic latency (ms) | 255.3 ± 80.9* | 220.8 ± 46.4 |
| Q-ratio of saccades (peak/mean velocity) | 2.37 ± 2.65* | 1.81 ± 0.39 |

*Statistically significant with a maximum p < 0.01
Mean ± standard deviation

At the time of testing, 45 patients (75%) were medicated for tremor and benefitted from single agents: 21 (35%) were receiving topiramate, 12 (20%) a β-blocker, and 12 (20%) primidone. Of the 15 untreated patients, 8 subsequently initiated treatment and all exhibited improvement of clinical symptoms at follow-up examinations.

Binocular horizontal and vertical eye position were recorded at 500 Hz using a video based eye tracker (Eyelink II, SR Research Ltd) with a reported resolution of 0.01° root mean square (RMS). The system tracks the center of the dark pupil utilizing infrared light and two cameras placed just below each eye, beyond the field of vision. The eye tracker system rests comfortably on the subject's head and is quick to setup and calibrate. To account for potential head movement, head position was recorded (at 125 Hz) with a six degree of freedom magnetic tracking system (trakSTAR, Ascension Technology Corp, Shelburne, Vt.) and synchronized with the eye position recordings.

Subjects were seated in a darkened room in front of a 26 inch diagonal LCD monitor placed 75 cm from their eyes and covering ±20° horizontally and ±13° vertically. The height of the monitor was adjusted so that the center of the screen corresponded to the center of the pupillary plane. Subjects were asked to fixate on a target stimulus and calibration and validation of the eye tracker was performed at three points along each of the cardinal axes, four times per subject, or until the reported gaze error was less that 0.5°. The target stimulus was a white dot sized to occupy 0.2° of visual angle on a black background. Eye and head position data were subsequently collected while subjects followed approximately 100 random and unpredictable discrete step changes in target position along the horizontal or vertical cardinal axes. Subjects were encouraged to close their eyes and rest between each recording to prevent fatigue. Patients were assessed while taking their prescribed medications.

Data were analyzed off line by a researcher blinded to the patient's diagnosis, using an interactive custom written plotting program (P.A.W). Fixations were analyzed for duration and stability. Saccades were analyzed for duration, peak velocity, acceleration, amplitude, and accuracy. Saccadic beginning and end points were determined by a velocity threshold set at 20°/sec and saccadic velocity was calculated by way of a two point central difference. Saccadic gain (accuracy) was calculated by the dividing the amplitude of the initial reflexive saccade by the amplitude of the target displacement. The main sequence, a well established method originally described by Bahill and colleagues,[10] was used to examine the relationship between the amplitude of a saccade and its duration and peak velocity. Additionally, Q-ratios (peak/mean velocities) were calculated. Normal values[11] are between 1.8 and 2.0 and values above 2.0 indicate single or multiple transient decelerations, with larger values signifying increasing amounts of deceleration.[12]

All statistical analysis was conducted using SPSS Statistics 17.0. For statistical analyses, α was set to 0.05. Data were assessed for normality using the Shapiro-Wilk test. Parameters that were not normally distributed (Q-ratio, saccadic duration at various amplitudes) were then log-transformed and confirmed to be log-normal distributions, and analysis was run on these values. Independent sample, unpaired, two-tailed t-tests were conducted to assess for differences between ET and control population data. Levene's test for the equality of variances was calculated and if the significance was found to be less than 0.05, equal variances were not assumed. In the later instance, a Welch's t-test was used to compare the means, which has the ability to compensate for samples of unequal variance. ANOVA were used to assess differences between different pharmaceutical therapies.

Results

Fixation Stability

Subjects with ET showed highly stable ocular fixations, comparable to controls. Root mean square (RMS) velocity, an excellent measure of ocular stability during fixation,[13] did not differ between subjects with ET (2.83±0.88) and controls (2.99±0.57, p=0.331). Head tremor was detected with the magnetic tracking system in two ET subjects. Large amplitude head tremor was readily evident clinically in one subject. In the other subject, head tremor was detected first with the magnetic tracking system, and upon clinical reevaluation, a subtle head tremor was noted. Due to potential activation of the vestibulo-ocular reflex, the data from those two subjects were excluded specifically from fixation stability analyses. Since head tremor would not affect other oculomotor parameters, data from these two subjects were included in subsequent analyses.

Figure 10:
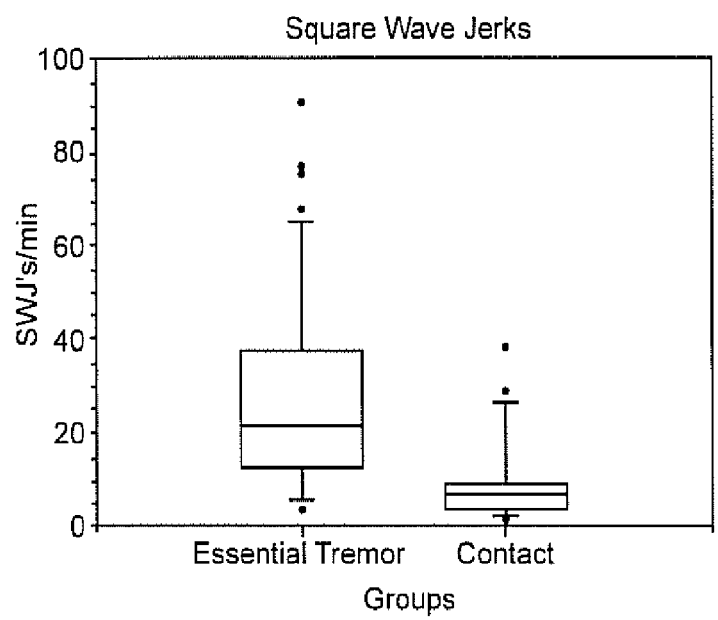
FIG. 10: Frequency of square wave jerks while fixating. ET patients exhibit appreciably more square wave jerks than age matched controls (p<0.0001). Middle bars inside boxes represent sample means, while the edges of boxes indicate first and third quartiles. Bottom and top bars represent minimum and maximum, respectively. Circles denote statistical outliers.
Figure 11:
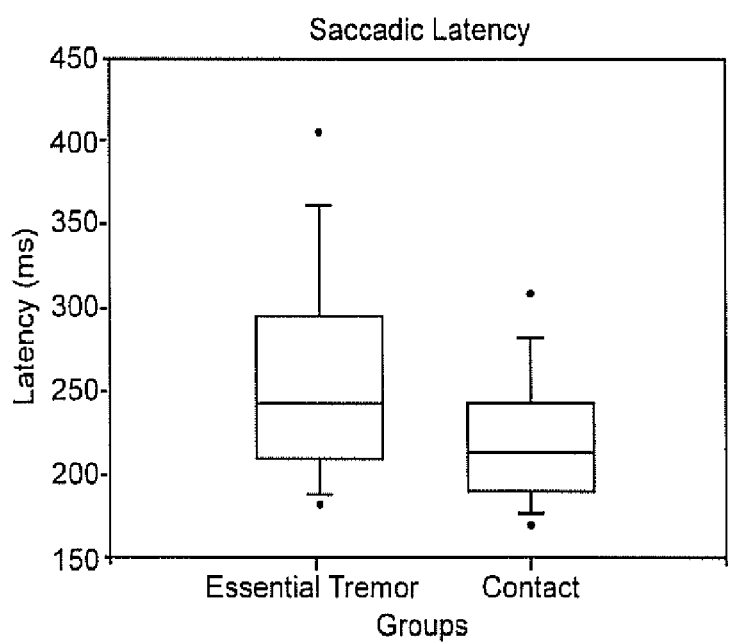
FIG. 11: Latency of reflexive saccades to randomly displaced targets. Patients with ET have increased saccadic latencies compared to age matched controls (p<0.01).

Although otherwise stable, the fixations of ET subjects were interrupted by an increased occurrence of square wave jerks (SWJ's, p<0.0001). During fixation, subjects with ET exhibited on average 26.9±20 SWJ's/min compared to 8.4±8.3 in controls (FIG. 10). Fundamental characteristics of the SWJ's, including mean amplitudes (0.62°±0.31, range: 0.13°-2.16° in ET subjects, 0.58°±0.23, range: 0.14°-1.56° for controls) and durations (257.8±89.1 ms, range: 72-536 ms for ET subjects, 265.6±91.3 ms range: 108-628 ms for controls) did not differ between patients and controls (p=0.19, and p=0.22 respectively).

Saccadic Dynamics

Latency.

Figure 12:
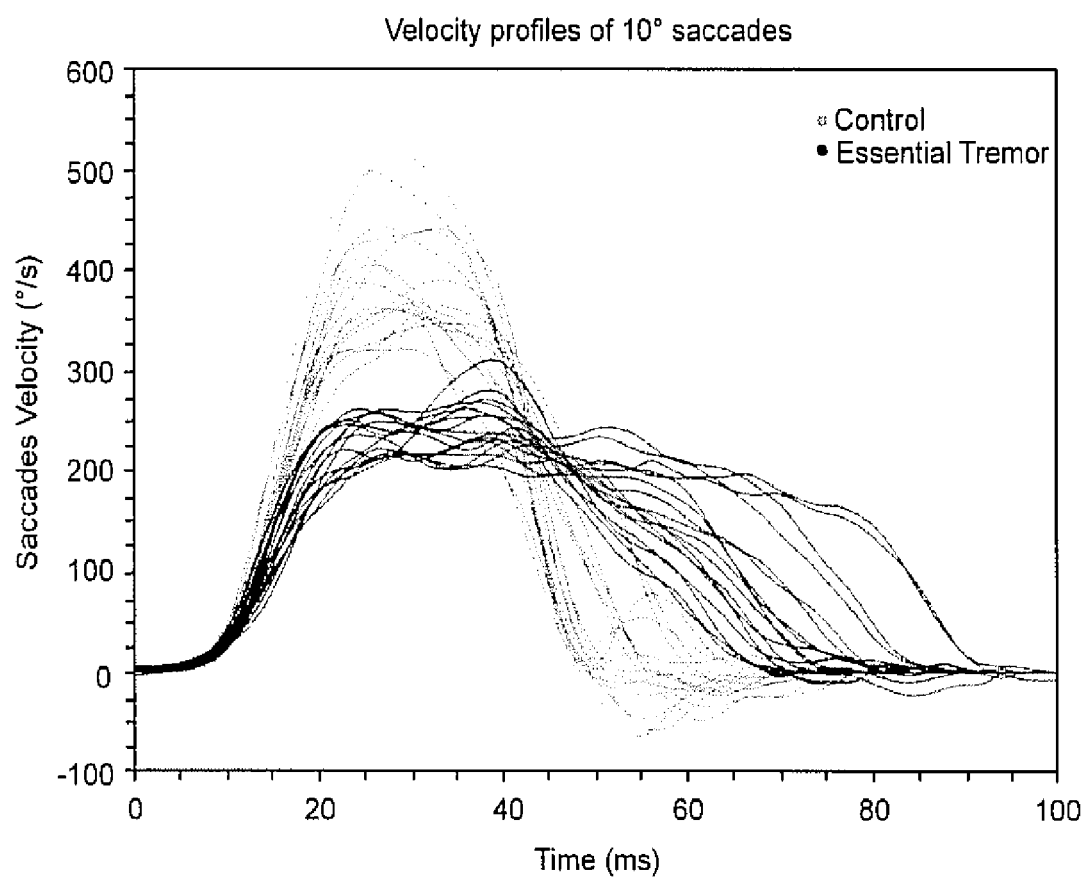
FIG. 12: Velocity profiles of 10° saccades. Single velocity traces are shown for 18 representative ET subjects and 18 control subjects. The velocity profiles were aligned at t=10 ms at the defined saccadic onset threshold (20°/s). Note the lower peak velocity, velocity plateau, and prolonged duration of saccades in ET subjects. The integral was taken of each individual velocity curve, and no difference was found between each group (p=0.59). This further supports that despite abnormal velocity behavior during saccadic flight, that subjects with ET maintain accurate saccadic amplitudes, and reach the intended target position.

Latency to initiate reflexive saccades was increased by a mean of 16.3% (p<0.01) in ET patients (255.3±80.9 ms) compared to controls (220.8±46.4 ms). FIG. 12 shows a boxplot of these differences.

Velocity and Duration.

Peak saccadic velocities were appreciably reduced and saccadic durations increased across ET subjects compared to controls. FIG. 12 shows examples of saccadic velocity profiles of study subjects, illustrating the normal, bell shaped, slightly positively skewed curves, with a single velocity peak in control subjects.[12] In contrast, ET subjects characteristically showed reduced peak velocities, and a lengthy fluctuating plateau of velocity, followed by slowed final decelerations. Using main sequence comparisons, a well established means to define saccadic differences,[10] Experimental data (not shown) demonstrated prominent reductions in peak saccadic velocities relative to saccadic amplitude in ET subjects compared to controls. While affecting all amplitudes, dynamic differences of saccades progressively increase as saccades become larger, with peak velocities for amplitudes of 30° or larger saccades reduced by 25.2% in ET subjects compared to controls (p<0.01). The divergent main sequence regression lines (data not shown) demonstrated progressively greater differences between ET subjects and controls in saccadic duration with increasing movement amplitude (31.8% for 30° or larger saccades, p<0.01). The Q-ratio of saccades (peak velocity/mean velocity), used to quantify and detect abnormalities of the velocity waveform of a saccade,[11] was on average 30.9% larger in ET subjects (2.37±2.65) than controls (1.81±0.39, p<0.001).

Accuracy.

Saccadic gain (amplitude of primary saccade/amplitude of target displacement) did not differ between ET subjects (0.95±0.08) and control subjects (0.95±0.09, p=0.297).

15 patients (25%) had SWJ's that were 2 S.D. above the control mean. 11 patients (18.3%) had latencies that were 2 S.D. above the control mean. 7 patients (11.6%) had a Q-Ratio that was 2 S.D. above the control mean. Of the above mentioned subjects with values more than 2 standard deviations from the control mean, none of those had both Q-Ratios and latencies 2 deviations away. However, 4 subjects had Q-Ratio and SWJ's that were both 2 standard deviations from the control mean, and 4 other subjects had latencies and SWJ's that were 2 standard deviations from the control mean. None of the subjects had all three categories 2 S.D. above the control mean. Of these patients with values 2 S.D. above the control mean, there was a very weak negative correlation between SWJ's and postural tremor scores ($R^2$: −0.14), with a slightly stronger negative correlation between SWJ's and action tremor (−0.21), There was no correlation between tremor scores and Q-Ratios or latencies.

All of the oculomotor measures were independent of disease duration, severity of tremor, and gender, both individually and as a group. Further, individual ANOVA, comparing de novo untreated, topiramate, primidone, and β-blocker treated subjects, show that differences in saccadic latencies (F=0.521, p=0.671), SWJ's (F=0.310, p=0.817), and Q-ratios (F=0.471, p=0.704) were not influenced by ET targeted therapies (post-hoc power analyses revealed power (1−β err prob)>0.999).

Discussion

The major finding in this study was that ET is associated with abnormalities in saccadic dynamics, including slowed peak velocities and prolonged durations. Additionally, ET subjects were observed to maintain stable fixations, which however are interrupted by more than triple the normal number of SWJ's. These abnormal oculomotor features were independent of disease duration and tremor severity. Furthermore, there were no differences in eye movement parameters between de novo untreated subjects and those taking tremor targeted medications, grouped together or by specific medications, suggesting that these abnormalities are inherent to the disease. To our knowledge, this is the first study to reveal appreciable saccadic abnormalities and increased SWJ's in ET.

In distinction from the highly efficient acceleration-deceleration movements observed in control subjects, saccades in ET subjects are characterized by lengthy, reduced, fluctuating peak velocities, and slowed final decelerations resulting in prolonged total movement times. Although present at all amplitudes, these saccadic abnormalities became progressively more evident as the amplitude of the saccade increased. Additionally, despite having abnormally altered movement dynamics, ET subjects, importantly, are nonetheless able to accurately capture step-displaced visual targets, as reflected by saccadic gains equal to that of normal controls, Finally, saccadic latencies were modestly prolonged in ET subjects by an average of 16.3% relative to control subjects.

In conflict with our findings, Helmchen and colleagues[5] found no abnormalities in saccadic latencies and velocities in ET subjects. The investigators however specifically assessed only 10° and 20° saccades rather than a continuum of amplitudes, analyzed only 20 saccades from 17 patients and 11 controls, and the main sequence and Q-ratios were not calculated. Conceivably, the comparatively greater statistical power in our study (~12,000 versus ~560 saccades) largely accounts for why we found differences in saccades, while Helmchen and colleagues did not. Although actual statistical values were unreported for the saccadic portion of that manuscript, their table possibly suggests that Helmchen et. al. had similar findings to this study, but the differences we subtle enough as to not reach significance. According to the values in their table, subjects with ET appeared to show lower peak saccadic velocities compared to controls, as well as slightly increased saccadic latencies in a subset of ET subjects with intention tremor. Additionally, ET subjects in their study appear to have normal saccadic gain, also consistent with our findings. Since all of the findings we report here are subtle changes from normal, we suggest that the discrepancies between the two reports are likely to be accounted for by differences in statistical power, despite similar results. Trillenberg et al.[6] reported that saccadic gain was normal in subjects with ET, which our findings confirm. Yet, in discrepancy with our study findings, the authors did not observe abnormalities in saccadic latency. Notably, Trillenberg and colleagues however only investigated a single saccade from each of just 12 subjects with ET.

The frequency of SWJ's has been previously reported to be increased in many neurological disorders and is generally attributed to cerebellar involvement.[14,15] Although ET subjects were observed presently to show more frequent SWJ's, their fixations were otherwise normally stable and therefore, would not necessarily be expected to be clinically relevant.[16] Additionally, the characteristics of individual SWJ's were not altered in ET subjects compared to controls.[16,17] Further, features of the SWJ's, apart from their frequency, are consistent with what has been reported in controls[17,18] and other disorders.[19]

In addition to the increased SWJ's, findings of transient slowing of saccades may support a principal role of cerebellar purkinje cells (PC) in the pathogenesis of ET. Although not uniformly found,[20,21] the prevailing pathological finding in ET brains has been reduced numbers of PCs, along with increased PC axonal swellings ("torpedoes").[22,23,24] Furthermore, in late onset Tay-Sachs (LOTS), in which PCs in the vermis appear to be largely destroyed,[25] saccades are similarly characterized by transient slowing of saccadic velocities;[26,27] albeit, more profoundly compared to ET cases. Moreover, findings of transient slowing of saccades in ET and LOTs are consistent with current theories suggesting that normally precisely timed inhibitory signals from PCs in the vermis "choke off" saccadic drive signals originating from the superior colliculus.[28,29]

The presently defined abnormal oculomotor dynamics in ET are distinctly different from those previously seen in Parkinson's disease (PD) using the same protocols.[13] In difference to the eye movement abnormalities in ET, subjects with PD exhibit normal latencies and movement dynamics during reflexive saccades. Further, PD subjects show normal frequencies of SWJ's, while exhibiting characteristic highly unstable, oscillatory fixations. Although unconfirmed,[30,31,32,33] this distinctive ocular tremor was suggested to be highly sensitive for distinguishing PD patients from control subjects.[13] Though the presently defined oculomotor abnormalities similarly largely distinguished subjects with ET from controls, there was nevertheless appreciable overlap between these two groups. One potential explanation for this overlap is that the present distinguishing ocular findings represent relative differences rather than being unique to those with ET. Another possibility is that since ET is likely to represent a heterogeneous disorder[34], those with the presently defined abnormal eye findings may represent a specific pathological subset of the disorder. Since SWJ's are a normal phenomenon, with appreciable overlap in frequencies among ET patients and healthy controls, slowed saccades are a primary feature of ET (as demonstrated herein), while an increased frequency of SWJ's is a secondary or supportive feature. As saccade velocity by itself cannot fully separate all controls from ET subjects, numbers of SWJ's, as well as saccadic latencies, can be helpful distinguishing features of ET. Particularly early in the course of the disease, differentiating between tremor due to ET versus PD can be difficult even for experienced movement disorder specialists.[35,36,37,38] However, since the oculomotor abnormalities in ET are distinctly different from those in PD, sensitive oculomotor testing will be valuable in differentiating these conditions.

Eye movements in ET are characterized by an increased frequency of SWJ's, which interrupt otherwise stable fixations, and by delayed initiation of saccades, with reduced, wavering peak velocities and prolonged, though accurate movements. While none of these features are of sufficient magnitude to be detectable on routine ophthalmological examinations,[39,40] the extent to which these abnormalities could potentially negatively impact normal visual function remains to be defined. The present study findings show that oculomotor testing is a valuable means to assist in the clinical differential diagnosis of ET.

ACKNOWLEDGEMENTS

Acknowledgments to Abu Qutubuddin M.D. (Physiatrist, Southeast PADRECC, McGuire Veterans Affairs Medical Center) and Peggy Roberge R.N. (Clinical Nurse Coordinator, Southeast PADRECC, McGuire Veterans Affairs Medical Center) for their assistance in recruiting subjects.

DISCLOSURES

This study was supported by the Department of Veterans Affairs.

All authors report no financial disclosure, commercial association, conflicts of interest, or competing interests.

REFERENCES

1. Zesiewicz T A, Chari A, Jahan 1, Miller A M, Sullivan K L. Overview of Essential Tremor. *Neuropsychiatric Disease and Treatment.* 2010:6. 401-08.
2. Deuschl G, Bain P, Brin M, Ad Hoc Scientific Committee. Consensus statement of the Movement Disorder Society on tremor. *Mov Disord.* 1998, 13(supplemental 3): 2-23.
3. Whaley N R, Putzke J D, Baba Y, et. al. Essential Tremor: phenotypic expression in a clinical cohort. *Parkinsonism and Related Disorders.* 2007:13. 333-39.
4. Louis E D, Ottoman R, Hauser W A. How common is the most common adult movement disorder? Estimates of the prevalence of essential tremor throughout the world. *Mov Disord.* 1998: 13(1). 5-10.
5. Helmchen C, Hagenow J, Miesner A, et. al. Eye movement abnormalities in essential tremor may indicate cerebellar dysfunction. *Brain* 2003: 126, 1319-32.
6. Trillenberg P, Führer J, Sprenger A, et. al. Eye-Hand Coordination in Essential Tremor. *Mov Disord.* 2006: 21(3); 373-79.
7. Straube A, Scheurer W, Eggert T. Unilateral cerebellar lesions affect initiation of ipsilateral smooth pursuit eye movements in humans. *Ann Neurol* 1997; 42: 891-98.
8. Moschner C, Crawford Ti, Heide W, Trillenburg P, Kömpf D, Kennard C. Deficits of smooth pursuit initiaion in patinets with degenerative cerebellar lesions. *Brain* 1999; 122: 2147-58.

9. Hain T C, Zee D S, Maria B E Tilt suppression of vestibulo-ocular reflex in patients with cerebellar lesions. *Acta Otolaryngol* 1988; 105; 13-20.
10. Bahill A T, Clark M R, Stark L. The Main Sequence, a tool for studying human eye movements. *Math Biosci* 1975; 24: 194.
11. Harwood M R, Mezey L E, Harris C M. The spectral main sequence of human saccades. *J Neurosci* 1999. 19:9098-106
12. Baloh R W, Konrad H R, Sills A W, Honrubia V. The Saccade Velocity Test. *Neurology* 1975: 25; 1071-76.
13. Gitchel G T, Wetzel P A, Baron M S, Pervasive Ocular Tremor in Parkinson's Disease. *Arch Neurol* 2012 August; 69(8): 1011-17
14. Rabiah P K, Bateman J B, Demer J L, et. al. Ophthalmologic findings in patients with cerebellar ataxia. *Am J Ophthalmol* 1997: 123, 108-17.
15. Garbutt S, Riley D E, Kumar A N, et. al. Abnormalities of optokinetic nystagmus in progressive supranuclear palsy. *J Neurol Neurosurg Psychiatry try*, 2004. 75: 1386-94.
16. Herishanu Y, Sharpe J A. Normal Square Wave Jerks. *Invest Ophthalmol Vis Sci* 1981, 20: 268-72.
17. Shallo-Hoffmann J, Sendler B, Muhlendyck H. Normal square wave jerks in differing age groups. *Invest Ophthalmol Vis Sci* 1990. 31: 1649-52.
18. Abadi R V, Gowen E. Characteristics of saccadic intrusions. *Vision Research.* 2004, 44: 2675-90.
19. Rascol O, Sabatini U, Simonetta-Moreau M, et. al. Square wave jerks in parkinsonian syndromes. *J Neurol Neurosurg Psychiatry,* 1991; 54: 599-602.
20. Rajput A H, Robinson C A, Rajput M L, Rajput A. Cerebellar purkinje cell loss is not pathognomonic of essential tremor. *Parkinsonism Relat Disord;* 2011 January: 17(1): 16-21.
21. Rajput A H, Robinson C A, Rajput M L, Robinson S L, Rajput A. Essential tremor is not dependent upon cerebellar purkinje cell loss. *Parkinsonism Relat Disord:* 2012 June; 18(5): 626-628.
22. Louis E D, Faust P L, Vonsattel J P, et. al. Neuropathological changes in essential tremor: 33 cases compared with 21 controls. *Brain.* 2007 December; 130(Pt 12): 3297-3307.
23. Axelrad J E, Louis E D, Honig L S, et. al. Reduced Purkinje cell number in essential tremor: a postmortem study. *Arch Neurol.* 2008 January; 65(1): 101-107.
24. Louis E D, Faust P L, Ma K J, Yu M, Cortes E, Vonsattel J P. Torpedoes in the Cerebellar Vermis in Essential Tremor Cases vs. Controls. *Cerebellum.* 2011; 10: 812-819.
25. Rucker J C, Leigh R J, Optican L M, Keller E L, Büttner-Ennever J A. Chapter 6.11. Ocular motor anatomy in a case of interrupted saccades. C. Kennard & R. J. Leigh (Eds.) *Progress in Brain Research. Vol* 171. Elsevier B.V.
26. Rucker J C, Shapiro B E, Han Y H, et. al. Neuroophthalmology of late-onset Tay-Sachs disease (LOTS). *Neurology,* 2004; 63: 1918-1926.
27. Rucker, J. C., S. H. Ying, W. Moore, et. al. 2011. Do brainstem omnipause neurons terminate saccades? In Basic and Clinical Ocular Motor and Vestibular Research. Janet Rucker & David S. Zee, Eds. *Ann. N.Y. Acad. Sci.* 1233: 48-57.
[28] Quaia C, Lefevre P, Optican L. M. Model of the control of saccades by Superior Colliculus and Cerebellum. *J Neurophysiol* 82: 999-1018, 1999.
[29] Optican L M, Quaia C. Distributed model of collicular and cerebellar functions during saccades. *Ann. N.Y. Acad. Sci.* 2002. 956:164-177.
30. Kaski D, Saifee T A, Buckwell D, Bronstein A M. Ocular Tremor in Parkinson's Disease Is Due to Head Oscillation. *Mov Disord.* 2013; 28(4): 534-537
31. Baron M S, Gitchel G T, Wetzel P A. Ocular Tremor in Parkinson's Disease is Due to Eye, not Head Oscillation. *Mov Disord.* 2013, epub ahead of print. doi: 10.1002/mds.25461
32. Leigh R J, Martinez-Conde S. Tremor of the Eyes, or of the Head, in Parkinson's Disease? *Mov Disord.* 2013, epub ahead of print. doi:10.1002/mds.25478
33. Duval, C. Ocular Tremor in Parkinon's Disease: The Debate is Not Over. *Mov Disord.* 2013. Epub ahead of print. doi: 10.1002/mds.25514
34. Benito-León 3, Louis E D. Update on essential tremor. *Minerva Med.* 2011; 102(6): 417-440.
35. Baumann C R. Epidemiology, diagnosis, and differential diagnosis in Parkinson's disease tremor. *Parkinsonism and Related Disorders,* 2012: 18(S1); S90-S92.
36. Shahed J, Jankovic J. Exploring the relationship between essential tremor and Parkinson's disease. *Parkinsonism and Related Disorder.* 2007: 13; 67-76.
37. Jain S, Lo S E, Louis E D. Common misdiagnosis of a common neurological disorder: how are we misdiagnosing essential tremor? *Arch Neural* 2006; 63: 1100-04.
38. Pahwa R, Lyons K E. Early Diagnosis of Parkinson's Disease: Recommendations From Diagnostic Clinical Guidelines. *Am J Manag Care.* 2010; 16: S94-S99.
39. Kumar A N, Han Y H, Liao K, et. al. Evaluating large saccades in patients with brain-stem or cerebellar disorders. *Ann N Y Acad Sci* 2005: 1039; 404-16.
40. Leigh R J, Kennard C. Using saccades as a research tool in the clinical neurosciences. *Brain* 2004; 127:460-77.

The invention claimed is:

1. A computer implemented method for diagnosing or confirming a diagnosis of Parkinson's disease, or for monitoring a treatment regimen of Parkinson's disease, comprising the steps of:
   detecting horizontal and vertical positions of one or both eyes of a subject in response to fixed and moving light stimulus using an eye tracking device;
   determining from data detected in said detecting step using one or more computers or computer networks, one or more values for saccadic measurements and one or more values of either or both fixation measurements or measurements associated with interruptions;
   comparing, using said one or more computers or computer networks,
      said one or more values for saccadic measurements with stored values or value ranges for subjects which suffer from Parkinson's disease, wherein said saccadic measurements include peak velocity and saccadic metrics; and
      said one or more values of either or both fixation measurements or measurements associated with interruptions with stored values or value ranges for subjects which suffer from Parkinson's, wherein said one or more values of either or both fixation measurements or measurements associated with interruptions include ocular tremor; and
   outputting at least one match for said subject based on said comparing step to either a normal response or to Parkinson's disease,
   wherein Parkinson's disease is diagnosed by presence of ocular tremor having a frequency ranging from 4.3 to 10.9 Hz and absence of abnormalities in peak velocity and absence of hypometric or hypermetric saccadic metrics.

2. The computer implemented method of claim 1, wherein said saccadic measurements further include latency.

3. The computer implemented method of claim 1, wherein said one or more values of either or both fixation measurements or measurements associated with interruptions further include one or more values selected from the group consisting of stable fixations, complex fixation instability, increased frequency fine amplitude chaotic tremor, chaotic fixations, vertical control, drift during fixation, increased frequency of square wave jerks, single pulse saccadic intrusions, double pulse saccadic intrusions, macro saccadic oscillations, and increased blink rate.

4. A computer implemented method for diagnosing or confirming a diagnosis of essential tremor, or for monitoring a treatment regimen of essential tremor, comprising the steps of:
   detecting horizontal and vertical positions of one or both eyes of a subject in response to fixed and moving light stimulus using an eye tracking device;
   determining from data detected in said detecting step using one or more computers or computer networks, one or more values for saccadic measurements and one or more values of either or both fixation measurements or measurements associated with interruptions;
   comparing, using said one or more computers or computer networks,
      said one or more values for saccadic measurements with stored values or value ranges for subjects which suffer from essential tremor, wherein said saccadic measurements include peak velocity; and
      said one or more values of either or both fixation measurements or measurements associated with interruptions with stored values or value ranges for subjects which suffer from essential tremor, wherein said one or more values of either or both fixation measurements or measurements associated with interruptions include ocular tremor and increased frequency of square wave jerks; and
   outputting at least one match for said subject based on said comparing step to either a normal response or to essential tremor,
   wherein essential tremor is diagnosed by absence of ocular tremor and presence of a slowing of saccadic velocity with a wavering plateau of velocity.

5. The computer implemented method of claim 4 wherein essential tremor is further diagnosed by presence of 6.9-46.9 square wave jerks per minute.

6. The computer implemented method of claim 4 wherein essential tremor is further diagnosed by an increased ratio of the peak velocity relative to an average velocity.

7. The computer implemented method of claim 4, wherein said saccadic measurements further include at least one of latency and saccadic metrics.

8. The computer implemented method of claim 4, wherein said one or more values of either or both fixation measurements or measurements associated with interruptions further include one or more values selected from the group consisting of stable fixations, complex fixation instability, increased frequency fine amplitude chaotic tremor, chaotic fixations, vertical control, drift during fixation, single pulse saccadic intrusions, double pulse saccadic intrusions, macro saccadic oscillations, and increased blink rate.

\* \* \* \* \*